(12) United States Patent
Beaulieu et al.

(10) Patent No.: US 9,663,551 B2
(45) Date of Patent: May 30, 2017

(54) SOLANIDINE-DERIVED COMPOUNDS

(71) Applicants: UNIVERSITÉ DE PICARDIE JULES VERNE, Amiens (FR); SEMENCES INNOVATION PROTECTION RECHERCHE ET ENVIRONMENT, Achicourt (FR)

(72) Inventors: Rémi Beaulieu, Achicourt (FR); Jacques Attoumbre, Achicourt (FR); Virginie Gobert-Deveaux, Achicourt (FR); Eric Grand, Amiens (FR); Imane Stasik, Amiens (FR); José Kovensky, Amiens (FR); Philippe Giordanengo, Amiens (FR)

(73) Assignees: UNIVERSITÉ DE PICARDIE JULES VERNE (FR); SEMENCES INNOVATION PROTECTION RECHERCHE ET ENVIRONMENT (FR)

( * ) Notice: Subject to any disclaimer, the term of this patent is extended or adjusted under 35 U.S.C. 154(b) by 0 days.

(21) Appl. No.: 14/905,928

(22) PCT Filed: Jul. 21, 2014

(86) PCT No.: PCT/FR2014/051871
§ 371 (c)(1),
(2) Date: Jan. 18, 2016

(87) PCT Pub. No.: WO2015/008007
PCT Pub. Date: Jan. 22, 2015

(65) Prior Publication Data
US 2016/0152659 A1    Jun. 2, 2016

(30) Foreign Application Priority Data

Jul. 19, 2013   (FR) ...................................... 13 57153

(51) Int. Cl.
| | | |
|---|---|---|
| *C07J 71/00* | (2006.01) | |
| *C07H 15/26* | (2006.01) | |
| *C07D 487/04* | (2006.01) | |
| *A01N 43/707* | (2006.01) | |

(52) U.S. Cl.
CPC ........ *C07J 71/0042* (2013.01); *A01N 43/707* (2013.01); *C07D 487/04* (2013.01); *C07H 15/26* (2013.01)

(58) Field of Classification Search
CPC .................................................... C07J 71/0042
USPC .................................... 514/176; 540/49, 58
See application file for complete search history.

(56) References Cited

FOREIGN PATENT DOCUMENTS

| WO | WO 98/58543 A1 | 12/1998 |
| WO | WO 01/49279 A2 | 7/2001 |
| WO | WO 2011/068987 A2 | 6/2011 |

OTHER PUBLICATIONS

International Search Report dated Sep. 19, 2014 issued in corresponding International patent application No. PCT/FR2014/051871.
Written Opinion dated Sep. 19, 2014 issued in corresponding International patent application No. PCT/FR2014/051871.
Gomah E. Nenaah: "Toxic and antifeedant activities of potato glycoalkaloids against Trogoderma granarium (Coleoptera: Dermestidae)", Journal of-Stored Products Research, vol. 47, No. 3, Jul. 1, 2011, pp. 185-190, XP055088298.

*Primary Examiner* — Brenda Coleman
(74) *Attorney, Agent, or Firm* — Ostrolenk Faber LLP

(57) ABSTRACT

Novel solanidine-derived compounds, the synthesis method thereof and the uses of same in the fields of phytosanitary protection and health. In particular, the novel compounds have toxic and/or repellent properties in relation to aphids, as well as other properties.

14 Claims, 2 Drawing Sheets

SOLANIDINE-DERIVED COMPOUNDS

CROSS REFERENCE TO RELATED APPLICATIONS

The present application is a 35 U.S.C. §371 National Phase conversion of PCT/FR2014/051871, filed Jul. 21, 2014, which claims benefit of French Application No. 1357153, filed Jul. 19, 2013, the disclosure of which is incorporated herein by reference. The PCT International Application was published in the French language.

TECHNICAL FIELD OF THE INVENTION

The present invention concerns novel compounds derived from glycoalkaloids, the method for synthesizing same, and uses thereof in particular in the fields of phytosanitary protection and health. In particular, the present invention concerns novel compounds having toxic and/or repellent properties with respect to aphids, as well as other properties.

BACKGROUND OF THE INVENTION

Glycoalkaloids are natural molecules metabolized exclusively by plants. Although certain of these molecules can be isolated from plants of the family Liliaceae, they are mostly found in the family Solanaceae, which comprises crop species such as potato, eggplant and tomato.

The growth of the potato industry is accompanied by an inevitable increase in the amount of coproducts produced. The management of this waste is at once an environmental, economic and regulatory issue. Today, the coproducts of this industry are mainly exploited in animal feed. It is thus essential to unlock the potential of this biomass for other industries and to increase their added value.

The potato biosynthesizes glycoalkaloids such as chaconine and solanine, which are found in significant amounts in industrial coproducts. These are secondary metabolites that provide the plant with natural protection against attacks from phytopathogens. They are notably effective against aphids, beetles, leafhoppers, nematodes and fungi.

Chaconines and solanines have a cytotoxic activity by acting on the cell membrane. Two mechanisms of action have been proposed: an action of lysing the membrane itself and an action of inhibiting transmembrane transport. Moreover, they have the ability to inhibit two enzymes essential to nerve transmission, i.e., acetylcholinesterase (AChe) and butyrylcholinesterase (BuChe).

Although they have excellent efficacy against pests, some species have developed mechanisms of resistance to such glycoalkaloids.

SUMMARY OF THE INVENTION

The present invention was carried out with respect to the prior art described above, and the objective of the present invention is not only to obtain novel compounds that are more effective than natural glycoalkaloids and have improved stability and biochemical properties, but also to provide a novel method for producing said compounds. Moreover, another objective of the present invention is to discover novel uses for such compounds.

With the objective of solving this problem, the present invention proposes a compound of formula (I):

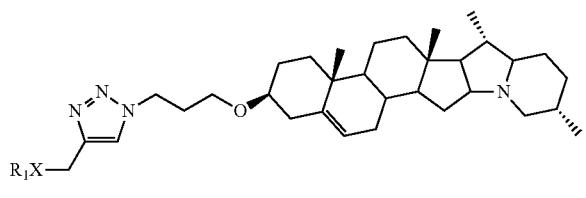

(I)

wherein X is an oxygen atom or a sulfur atom, and $R_1$ represents a group comprising 1 to 10 saccharide unit(s), each saccharide unit corresponding to any hexose or any pentose. Each saccharide unit is selected independently.

In the context of the present invention, by "group comprising 1 to 10 saccharide unit(s)" is meant a group formed by a combination of 1 to 10 substituted or unsubstituted monosaccharide molecules. The monosaccharide molecules are linked together by an O-glycosidic linkage or an S-glycosidic linkage. Preferably, all the monosaccharide molecules are linked together by an O-glycosidic linkage.

Preferably, said saccharide unit is a hexose.

Preferably, $R_1$ is a hexosyl group. Advantageously, $R_1$ is selected from the group consisting of a glucosyl, a galactosyl and a rhamnosyl.

Preferably, $R_1$ comes from a monosaccharide, a disaccharide, a thiodisaccharide, a trisaccharide or a thiotrisaccharide.

Thus, a feature of the invention rests in the employment of a novel linker between the various saccharide motifs and solanidine. Thanks to this feature, the compound according to the invention has enhanced stability and biochemical properties. The present Inventors discovered that the linker according to the invention could have several roles. The first would be to move the saccharide moiety sufficiently far from the aglycone moiety responsible for the activity. When these two moieties are very close, steric hindrance can limit the inhibitory activity on enzymes. It is thus possible to avoid reduced reactivity due to steric hindrance. The second role would be to provide the compounds with flexibility. Indeed, chaconine and solanine are rather rigid molecules, and to provide flexibility would be advantageous in terms of cytotoxic activity. Thanks to this flexibility, a glycoalkaloid consisting of a monosaccharide, a disaccharide or a thiodisaccharide could suffice to produce membranolytic properties (already shown in the literature). Moreover, triazole is more stable in biological fluids than most other linkages used as linkers.

Preferably, X is an oxygen atom or a sulfur atom.

According to the present invention, by "hexose" is meant cyclic compounds of chemical formula $C_6H_{12}O_6$ such as glucose and galactose, or cyclic deoxyhexoses of chemical formula $C_6H_{12}O_5$ such as rhamnose and fucose.

According to the present invention, by "pentose" is meant cyclic compounds of chemical formula $C_5H_{10}O_5$ such as arabinose, ribose or xylose, or cyclic deoxypentoses of chemical formula $C_5H_{10}O_4$ such as deoxyribose.

In the context of the present invention, the "disaccharide" is formed by combining two monosaccharide molecules. Both monosaccharides are linked together by an osidic linkage. For example, the disaccharide can be sucrose, maltose or lactose.

In the context of the present invention, the "trisaccharide" is formed by a combination of three monosaccharide molecules linked together by an osidic linkage. For example, the trisaccharide can be chacotriose or solatriose.

In the context of the present invention, the "thiodisaccharide" is formed by a combination of two monosaccharide molecules linked together by an S-glycosidic linkage.

In the context of the present invention, the "thiotrisaccharide" is formed by a combination of three monosaccharide molecules wherein at least two monosaccharide molecules are linked together by an S-glycosidic linkage.

The present invention also concerns an intermediate compound of formula (II):

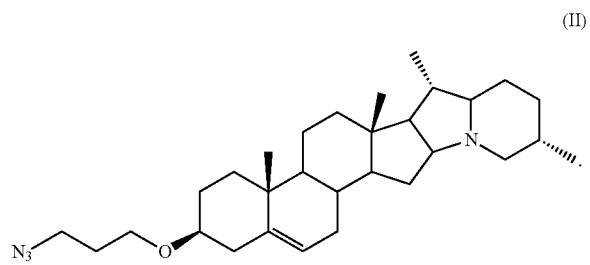 [SMILES: C[C@H]1CCC2[C@@H](C)C3C(CC4C5CC=C6C[C@@H](OCCCN=[N+]=[N-])CC[C@]6(C)C5CC[C@@]43C)N2C1]

(II)

Thus, the compounds of formula (I) according to the invention can be obtained from this compound.

The present invention also concerns various uses of the compound of formula (I). Preferably, the compound of formula (I) is used as an insecticide. The compound according to the invention can in particular be used as an aphicide. Moreover, the compound of formula (I) can also be used in compositions as an antibacterial, antifungal, nematicide or antiviral.

The compound of formula (I) as defined above can be used as a medicine. It is in particular used as an anticancer, antibiotic or antiviral agent. In this case, it can be comprised in a pharmaceutical composition that can optionally comprise one or more pharmaceutically acceptable excipients. This pharmaceutical composition comprises an effective amount of at least one compound according to the present invention, or a pharmaceutically acceptable salt, hydrate or solvate of said compound, and at least one pharmaceutically acceptable excipient. Said excipient is selected, according to the desired dosage form and mode of administration, from the excipients known to persons skilled in the art.

The present invention further comprises a method for obtaining the compound of formula (I). According to the invention, the process comprises the following steps:

a) there is provided said compound of formula (II):

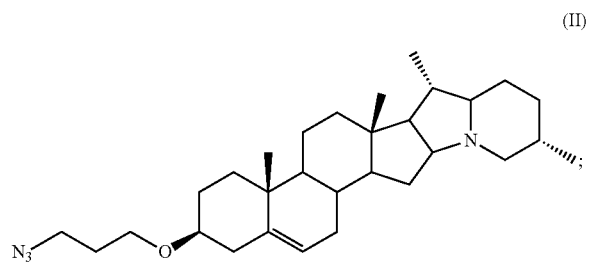 [SMILES: C[C@H]1CCC2[C@@H](C)C3C(CC4C5CC=C6C[C@@H](OCCCN=[N+]=[N-])CC[C@]6(C)C5CC[C@@]43C)N2C1]

(II)

and b) said compound of formula (II) is reacted, in the presence of a catalyst, with a compound of formula (III):

(III)

wherein $R_1$ is as defined above.

Thus, the present Inventors developed the coupling between the saccharide moiety (compound III) and the aglycone moiety (compound II).

With regard to step (a), the compound of formula (II), i.e., 3-O-(3-azidopropyl)solanidine, is prepared by a suitable method.

As for step (b), the catalyst is selected from ruthenium compounds or copper compounds. Preferably, the coupling by copper-catalyzed azide-alkyne cycloaddition (CuAAC) is carried out according to one of the methods described by Sharpless (Sharpless et al., *Angew. Chem. Int. Ed.* 2002, 41(14), 2596-2599) and Meldal (Meldal et al., *J. Org. Chem.* 2002, 67(9), 3057-3064). This azide-alkyne cycloaddition has many advantages in terms of reactivity. It is compatible with many chemical functions, it is perfectly regioselective, it does not lead to the formation of any secondary products and in general provides high yields. When the CuAAC coupling method described by Meldal is used for the synthesis (according to Zhang et al., *Synthetic Commun.* 2009, 39(5), 830-844), it is essential to use an organic solvent such as toluene or THF. In these solvents, the solubility of free sugars (unsubstituted hydroxyls) is limited, making it necessary to carry out the coupling on protected sugars (hydroxyls substituted with protecting groups). In contrast, when the CuAAC coupling method described by Sharpless et al. is used to synthesize glycosteroids (according to Rivera et al., *Tetrahedron* 2011, 67(40), 7713-7727), a mixture of organic solvent and water is needed to reduce copper(II) to copper (I). The presence of water also makes it possible to solubilize free sugars very easily. The protecting groups are thus cleaved before the CuAAC. The method described by Sharpless uses copper(II), in a stoichiometric amount, which is reduced to copper(I) in situ using sodium ascorbate. The method described by Meldal uses copper(I) directly but in a catalytic amount. Advantageously, the catalyst is selected from copper(II) salts; preferably, the catalyst is $CuSO_4$.

Moreover, it is preferable to purify the glycoalkaloids after step b). The compounds according to the invention can be purified by centrifugal partition chromatography (CPC).

Even more advantageously, the method for obtaining the compound of formula (I) further comprises the following steps:

c) there is provided said compound of formula (IV):

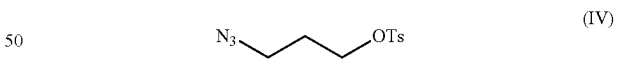

(IV)

wherein Ts is a tosyl group;

d) there is provided a compound of formula (V):

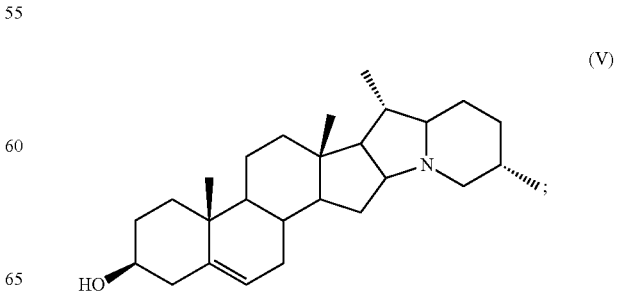

(V)

and
  e) the compound of formula (IV) is reacted with the compound of formula (V) in order to obtain the compound of formula (II).

The compound of formula (V), i.e., solanidine, is obtained by a suitable method known to persons skilled in the art. It can be obtained from chaconine or solanine, for example. Chaconines and/or solanines extracted from coproducts of the potato industry are hydrolyzed. Once the saccharide moiety is removed by hydrolysis, solanidine can be purified by CPC.

Given that solanidine extracted from coproducts is available only in small amounts, there has been a genuine need to provide a method for obtaining the compound of formula (II) with a relatively large yield. Thanks to the method according to the invention, the yield of the compound of formula (II) can reach more than 70%. The compound of formula (IV) can be coupled with the compound of formula (V) under conditions defined by persons skilled in the art.

The present invention also concerns a composition comprising the compound of formula (I). In this case, the composition comprises at least 0.001 mM, preferably 0.001 to 2 mM, of the compound of formula (I).

The present invention further comprises a compound of formula (VI):

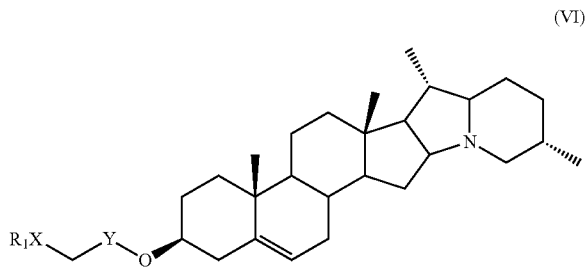

(VI)

wherein: $R_1$ and X are as defined above; and Y represents a chain of atoms able to connect (V) and $XR_1$. Y can be selected from the group consisting of one or more methylenes, $(-CH_2-)_n$, wherein n=1 to 20, one or more ethylene glycol(s), $(-C_2H_4O-)_n$, wherein n=1 to 20, and one of the substituents of formulas (VII) to (IX):

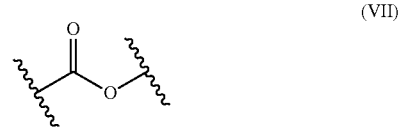

(VII)

(VIII)

(IX)

BRIEF DESCRIPTION OF THE DRAWINGS

Other features and advantages of the invention will become apparent on reading the following description of a specific embodiment of the invention, given by way of illustration in a non-limiting manner, in reference to the accompanying drawings wherein.

DESCRIPTION OF EMBODIMENTS

Figure 1A:
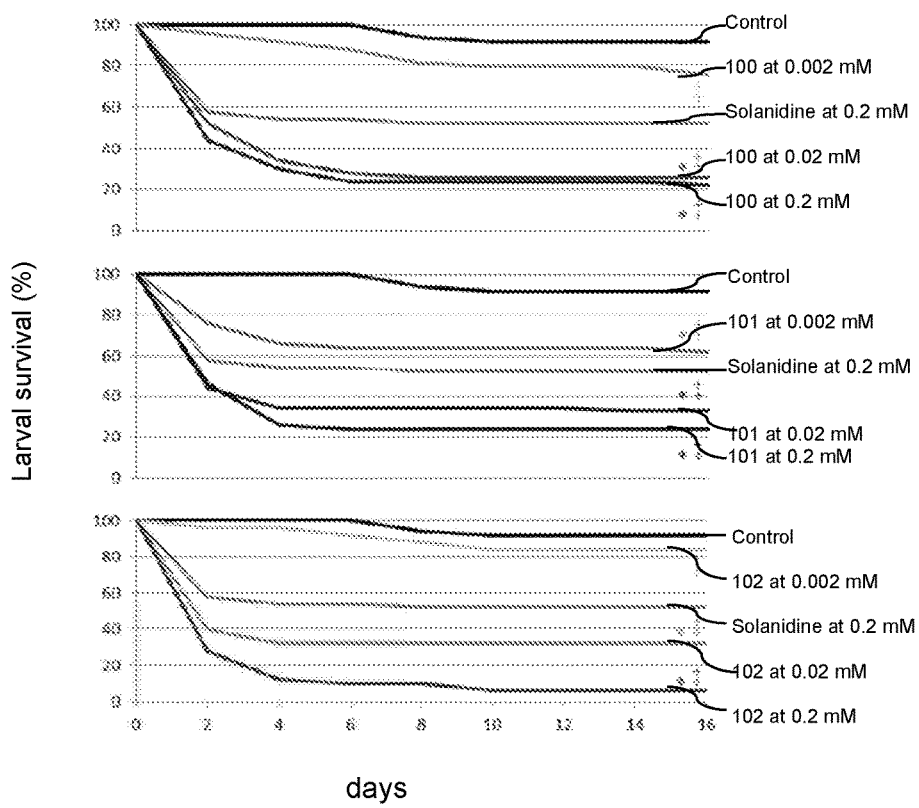
FIG. 1A shows the effects of the compounds according to the invention (compounds 100, 101 and 102) on *Macrosiphum euphorbiae* larvae survival, wherein the results were analyzed using Pearson's $X^2$ test; $\alpha=0.05$; *=significantly different from the control; ‡=significantly different from 0.2 mM solanidine.

Example 1 Preparation of Compounds According to the Invention 1-1. Chemical Materials and Methods a) Reagents and Solvents The reagents used come from the companies Sigma-Aldrich, Acros and Alfa Aesar and are employed without purification. The anhydrous solvents, except for dichloromethane and THF, are purchased in the Acroseal® format from Acros. Dichloromethane is distilled under an inert atmosphere in the presence of calcium hydride. THF is distilled under an inert atmosphere in the presence of sodium and benzophenone.

b) Chromatography

Thin-Layer Chromatography (TLC)

Thin-layer chromatography was carried out on silica plates with Merck 60 $F_{254}$ aluminum support. The techniques used to reveal the products after elution are:

for the saccharide derivatives: $H_2O/96\%$ $H_2SO_4/(NH_4)_4Ce(SO_4)_2.2H_2O/(NH_4)_6Mo_7O_{24}.4H_2O$ (188 ml/12 ml/2.1 g/5.3 g) and then heating.

for the solanidine derivatives: Dragendorf's reagent according to Munier and Macheboeuf.

Solution A: dissolve 0.85 g of bismuth nitrate in 10 ml of acetic acid and 40 ml of water.

Solution B: dissolve 8 g of potassium iodide in 20 ml of water.

Vaporization solution: solution A/solution B/AcOH/$H_2O$ (1 ml:1 ml:4 ml:20 ml).

Conventional Flash Chromatography

Conventional purifications are carried out using glass columns filled with silica gel (GERUDAN GERURAN SI 60, 0.040-0.062 mm particle size, Merck). The crude reaction product is dissolved in a minimum of solvent in order to be introduced at the top of the column or to be adsorbed on silica and then introduced at the top of the column. The elution is achieved by passing an elution gradient under air pressure (0.8 bar).

Automated Flash Chromatography

Automatic flash purifications were performed using the Reveleris® iES Flash System (Grace). Separation is accomplished using commercially available prepacked columns of silica or C-18 (4 g, 12 g, 24 g, 40 g, 80 g). The purifications can be normal phase or reversed phase. The mass of the purifiable products corresponds to at most 10% of the mass of the silica of the prepacked column. The purifications are carried out at a mean pressure of 50 psi (which may be up to 200 psi). This system is equipped with a light-scattering detector (LSD) and an adjustable dual-wavelength UV detector.

Centrifugal Partition Chromatography (CPC)

The purifications were carried out by centrifugal partition chromatography using an Armen® CPC 250 system connected to an Armen® LS-5600 collector. This is a semi-preparative system into which up to 6 g of crude product can be injected. The products are separated according to their partition coefficient in a given mixture of biphasic solvents. When the heavy phase is held stationary as the mobile phase is continuously injected, this is called ascending mode. The reverse is called descending mode. The system is equipped with a UV-visible detector.

As for solanidine, the purification is carried out in ascending mode in a biphasic mixture of $H_2O$/BuOH/AcOEt (50:7.5:42.5). Centrifugation is carried out at 3000 rpm.

c) Characterization of the Compounds

Specific Optical Rotation

The specific optical rotation measurements are made at a temperature of 20° C. using the Perkin-Elmer 343 polarimeter, which emits polarized light at a wavelength (A) of 549 nm (sodium D line). Concentrations c are expressed in grams per 100 ml of solvent.

Melting Point

Melting points were measured using a Büchi 535 automatic apparatus with a maximum temperature of 275° C.

Infrared Spectrometry

Infrared spectrometry analyses are carried out on a Shimadzu® FTIR-84005 spectrometer. Measurements are recorded using the ATR technique with the IR Solution software and the values of the bands obtained are expressed in $cm^{-1}$.

Low-Resolution Mass Spectrometry

Low-resolution mass spectrometry analyses are carried out on a single-quadrupole device (Micromass ZQ, Waters) having an electrospray ionization source (Z-spray). This apparatus allows the use of positive- or negative-ion mode. The capillary voltage is 3.5 kV and the cone voltage was varied between |20| and |120| V. The source and desolvation temperatures are 80 and 150° C., respectively. The desolvation/nebulization gas is nitrogen.

High-Resolution Mass Spectrometry

High-resolution mass spectrometry (HRMS) analyses are performed on a hybrid quadrupole time-of-flight mass spectrometer (Micromass Q-TOF Ultima Global, Waters) equipped with an electrospray ionization source. The source and desolvation temperatures are 80 and 120° C., respectively. The gas used for nebulization and desolvation is nitrogen at flow rates of 20 and 500 l/h, respectively. The capillary voltage is 3.5 kV and the cone voltage was varied between 100 and 250 V. Before any measurement of exact mass, a calibration with orthophosphoric acid is carried out. Since the precision of the Q-TOF measurement of exact mass is below 5 ppm, it is possible to access the elemental composition of the molecules.

NMR Spectrometry

The $^1H$ NMR and $^{13}C$ NMR spectra are recorded using two NMR spectrometers. The first is a Bruker Avance 300 spectrometer. The $^1H$ NMR spectra are recorded at 300 MHz and the $^{13}C$ NMR spectra at 75 MHz. A 5 mm QNP probe is used. The second is a Bruker Avance 600 spectrometer. In this case, the $^1H$ NMR spectra are recorded at 600 MHz and the $^{13}C$ NMR spectra at 150 MHz. A 5 mm TXi probe is used. All the experiments were carried out at a temperature of about 25° C. in deuterated solvent, which also serves as a reference, except for $D_2O$ where a drop of methanol is used as the reference for $^{13}C$ NMR (see Table 1 below). Chemical shifts are given in ppm. Coupling constants are expressed in hertz. The NMR spectra are processed using TopSpin or MestReNova.

TABLE 1

| Reference chemical shifts (in ppm). | | |
|---|---|---|
| | $^1H$ | $^{13}C$ |
| $CDCl_3$ | 7.26 | 77.16 |
| $D_2O$ | 4.79 | 49.50 (MeOH) |
| Pyridine-$d_5$ | 7.22/7.58/8.74 | 123.87/135.91/150.35 |

General Numbering of Carbons:

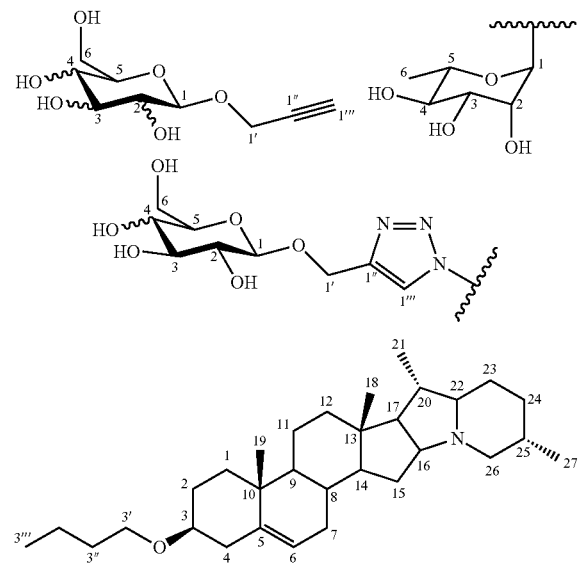

1-2. Preparatory Steps

Compound 2: propargyl 2,3,4,6-tetra-O-acetyl-3-D-glucopyranoside of formula

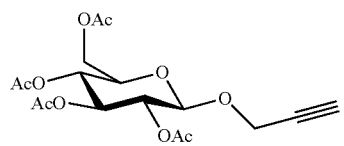

1,2,3,4,6-Penta-β-acetyl-6-D-glucopyranose (25.62 mmol, 10.0 g) is dissolved in anhydrous dichloromethane (3.12 mol, 200 ml). The reaction medium is then placed under an inert atmosphere. Propargylic alcohol (30.72 mmol, 1.82 ml) and $BF_3.Et_2O$ (102.48 mmol, 12.64 ml) are added. The mixture is stirred for 2 hours, still under an inert atmosphere and at room temperature. Potassium carbonate (38.43 mmol, 5.31 g) is added and the mixture is stirred for 30 minutes. The reaction medium is filtered through sintered glass and the yellow filtrate collected is washed with 2×200 ml of distilled water. The aqueous phases are combined and extracted with 2×100 ml of dichloromethane. The organic phases are combined and dried over $MgSO_4$. The solvent is evaporated under reduced pressure. The solid obtained is dissolved in dichloromethane and then crystallized by adding cyclohexane until cloudy. The mixture is stirred for 20 minutes and then filtered through sintered glass. The crystallization is repeated twice. The white solid obtained is dried in a desiccator overnight. Compound 2 is thus obtained with a yield of 84% (8.3 g).

Appearance: white solid
M: 386.35 g·mol$^{-1}$
Empirical formula: $C_{17}H_{22}O_{10}$
Rf: 0.32 (toluene/AcOEt: 75:25)
Mp: 114-115° C.
$[\alpha]_D^{20}$: −43.2° (c=1, $CHCl_3$)
ESI-MS (M+Na$^+$): 409
FT-IR (ATR in cm$^{-1}$): 3273 (uC≡H), 1753-1732 (uC=O), 1232-1207 (uC—O), 1037 (uC—O)

$^1$H NMR ($CDCl_3$, 300 MHz) δ 5.19 (t, 1H, $^3J_{3,2}=^3J_{3,4}=$ 9.6 Hz, $H_3$), 5.05 (t, 1H, $^3J_{4,3}=^3J_{4,5}=$9.6 Hz, $H_4$), 4.96 (dd, 1H, $^3J_{2,3}$=9.6 Hz, $^3J_{2,1}$=7.8 Hz, $H_2$), 4.73 (d, 1H, $^3J_{1,2}$=7.8 Hz, $H_1$), 4.32 (d, 2H, $^4J_{1',1'''}$,=2.4 Hz, $H_{1'}$), 4.23 (dd, 1H, $^2J_{6a,6b}$=12.3 Hz, $^3J_{6a,5}$=4.5 Hz, $H_{6a}$), 4.09 (dd, 1H, $^2J_{6b,6a}$=12.3 Hz, $^3J_{6b,5}$=2.4 Hz, $H_{6b}$), 3.69 (ddd, 1H, $^3J_{5,4}$=9.6 Hz, $^3J_{5,6a}$=4.5 Hz, $^3J_{5,6b}$=2.4 Hz, $H_5$), 2.45 (t, 1H, $^4J_{1''',1'}$=2.4 Hz, $H_{1'''}$), 2.04-1.96 (4s, 12H, $CH_3CO_2$)

$^{13}$C NMR ($CDCl_3$, 75 MHz) δ 170.64-169.42 ($CH_3\underline{C}O_2$), 98.16 ($C_1$), 78.16 ($C_{1''}$), 75.59 ($C_{1'''}$), 72.78 ($C_3$), 71.94 ($C_5$), 70.98 ($C_2$), 68.33 ($C_4$), 61.79 ($C_6$), 55.96 ($C_{1'}$), 20.73-20.61 ($\underline{C}H_3CO_2$)

Compound 3: propargyl β-D-glucopyranoside of formula

Compound 2 (23.0 mmol, 8.9 g) is dissolved in methanol (4.9 mol, 200 ml). A solution of sodium (20.0 mmol, 465 mg) in methanol (4.9 mol, 200 ml) is then added to the reaction medium. The mixture is stirred for 15 hours at room temperature. An ion-exchange resin (IR-120 [H]$^+$) is then added to a pH of 5-6. The reaction medium is filtered through sintered glass and the resin is washed with methanol. The solvent is evaporated under reduced pressure and the solid dried in a desiccator overnight. Compound 3 is obtained with a yield of 98% (4.9 g).

Appearance: white solid
M: 218.20 g·mol$^{-1}$
Empirical formula: $C_9H_{14}O_6$
Rf: 0.43 ($CH_2Cl_2$/MeOH: 80:20)
Mp: 54-55° C.
$[\alpha]_D^{20}$: −53.9° (c=2, $H_2O$)
ESI-MS (M+Na$^+$): 241
FT-IR (ATR in cm$^{-1}$): 3289 (uO—H), 3236 (uC≡H), 2874 (uC—H), 1365 (uC—O), 1026 (uC—O)

$^1$H NMR ($D_2O$, 300 MHz) δ 4.61 (d, 1H, $^3J_{1,2}$=8.1 Hz, $H_1$), 4.54 (dd, 1H, $^2J_{1'a,1'b}$=15.9 Hz, $^4J_{1'a,1'''}$=2.4 Hz, $H_{1'a}$), 4.48 (dd, 1H, $^2J_{1'b,1'a}$=15.9 Hz, $^4J_{1'b,1'''}$=2.4 Hz, $H_{1'b}$), 3.95 (dd, 1H, $^2J_{6a,6b}$=12.3 Hz, $^3J_{6a,5}$=2.2 Hz, $H_{6a}$), 3.76 (dd, 1H, $^2J_{6b,6a}$=12.3 Hz, $^3J_{6b,5}$=5.7 Hz, $H_{6b}$), 3.50 (m, 3H, $H_3$, $H_4$ and $H_5$), 3.33 (dd, 1H, $^3J_{2,1}$=8.1 Hz, $^3J_{2,3}$=9.0 Hz, $H_2$), 2.99 (t, 1H, $^4J_{1''',1'}$=2.4 Hz, $H_{1'''}$)

$^{13}$C NMR ($D_2O$, 75 MHz) δ 101.09 ($C_1$), 79.45 ($C_{1''}$), 76.98 ($C_{1'''}$), 76.51 ($C_3$, $C_4$ or $C_5$), 76.25 ($C_3$, $C_4$ or $C_5$), 73.42 ($C_2$), 70.10 ($C_3$, $C_4$ or $C_5$), 61.26 ($C_6$), 57.08 ($C_{1'}$)

Compound 5: propargyl 2,3,4,6-tetra-O-acetyl-β-D-galactopyranoside of formula 1,2,3,4,6-Penta-O-acetyl-β-D-galactopyranose (12.81 mmol, 5.0 g) and silver trifluoroacetate (19.21 mmol, 4.28 g) are placed under an inert atmosphere. Anhydrous dichloromethane (2.34 mol, 150 ml) is added, followed by propargylic alcohol (19.21 mmol, 1.13 ml) and tin chloride (38.43 mmol, 4.5 ml). The solution is stirred under an inert atmosphere at room temperature for 1.5 hours. The reaction medium is diluted by adding 400 ml of dichloromethane and then washed successively with 300 ml of saturated $NaHCO_3$ solution, 3×300 ml of distilled water and finally 300 ml of saturated NaCl solution. The organic phase is dried over $MgSO_4$ and the solvents are evaporated under reduced pressure. The yellow syrup obtained is purified by conventional chromatography on silica gel with an AcOEt/cyclohexane (20:80 to 40:60) elution gradient. The residue is dried in a desiccator overnight. Compound 5 is thus obtained with a yield of 87% (4.3 g).

Appearance: White solid
M: 386.35 g·mol$^{-1}$
Empirical formula: $C_{17}H_{22}O_{10}$
Rf: 0.47 (cyclohexane/AcOEt: 50:50)
Mp: 66-68° C.
$[\alpha]_D^{20}$: −33.4° (c=1, $CHCl_3$)
ESI-MS (M+Na$^+$): 409
FT-IR (ATR in cm$^{-1}$): 3276 (uC≡H), 1741 (uC=O), 1212-1044 (uC—O)

$^1$H NMR ($CDCl_3$, 300 MHz) δ 5.30 (dd, 1H, $^3J_{4,3}$=3.4 Hz, $^3J_{4,5}$=1.0 Hz, $H_4$), 5.11 (dd, 1H, $^3J_{2,3}$=10.5 Hz, $^3J_{2,1}$=7.9 Hz, $H_2$), 4.96 (t, 1H, $^3J_{3,2}$=10.5 Hz, $^3J_{3,4}$=3.4 Hz, $H_3$), 4.65 (d, 1H, $^3J_{1,2}$=7.9 Hz, $H_1$), 4.28 (d, 2H, $^4J_{1',1'''}$=2.4 Hz, $H_{1'}$), 4.09 (dd, 1H, $^2J_{6a,6b}$=11.2 Hz, $^3J_{6a,5}$=6.6 Hz, $H_{6a}$), 4.04 (dd, 1H, $^2J_{6b,6a}$=11.2 Hz, $^3J_{6b,5}$=6.6 Hz, $H_{6b}$), 3.87 (dt, 1H, $^3J_{5,4}$=1.0 Hz, $^3J_{5,6}$=6.6 Hz, $H_5$), 2.43 (t, 1H, $^4J_{1''',1'}$=2.4 Hz, $H_{1'''}$), 2.06-1.89 (4s, 12H, $CH_3CO_2$)

$^{13}$C NMR ($CDCl_3$, 75 MHz) δ 170.13-169.29 ($CH_3\underline{C}O_2$), 98.49 ($C_1$), 78.15 ($C_{1''}$), 75.40 ($C_{1'''}$), 70.68 ($C_3$ or $C_5$), 70.64 ($C_3$ or $C_5$), 68.36 ($C_2$), 66.88 ($C_4$), 61.07 ($C_6$), 55.72 ($C_{1'}$), 20.58-20.37 ($\underline{C}H_3CO_2$)

Compound 6: propargyl β-D-galactopyranoside of formula

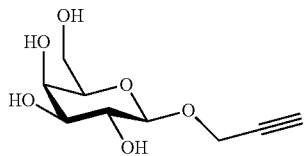

Compound 5 (11.13 mmol, 4.3 g) is dissolved in methanol (2.47 mol, 100 ml). A solution of sodium (10.0 mmol, 230 mg) in methanol (2.47 mol, 100 ml) is then added to the reaction medium. The mixture is stirred for 15 hours at room temperature. An ion-exchange resin (IR-120 [H$^+$]) is added to a pH of 5-6. The reaction medium is filtered through sintered glass and the resin is washed with methanol. The solvents are evaporated under reduced pressure and the residue obtained is dried in a desiccator overnight. Compound 6 is obtained with a yield of 91% (2.2 g).

Appearance: white solid
M: 218.20 g·mol$^{-1}$
Empirical formula: $C_9H_{14}O_6$
Rf: 0.28 (CH$_2$Cl$_2$/MeOH: 80:20)
Mp: 94-96° C.
[α]$_D^{20}$: −8.6° (c=0.25, H$_2$O)
ESI-MS (M+Na$^+$): 241
FT-IR (ATR in cm$^{-1}$): 3257 (uO—H), 3234 (uC≡H), 2938-2874 (uC—H), 1365-1294 (uO—H), 1044-1026 (uC—O)
$^1$H NMR (D$_2$O, 300 MHz) δ 4.59 (d, 1H, $^3J_{1,2}$=7.8 Hz, H$_1$), 4.53 (dd, 1H, $^2J_{1'a,1'b}$=15.9 Hz, $^4J_{1'a,1'''}$=2.5 Hz, H$_{1'a}$), 4.46 (dd, 1H, $^2J_{1'b,1'a}$=15.9 Hz, $^4J_{1'b,1'''}$=2.5 Hz, N$_{1'b}$), 3.95 (dd, 1H, $^3J_{5,4}$=0.3 Hz, $^3J_{5,6}$=3.5 Hz, H$_5$), 3.78 (m, 3H, H$_{6a}$, H$_{6b}$, H$_4$), 3.68 (dd, 1H, $^3J_{3,2}$=9.9 Hz, $^3J_{3,4}$=3.5 Hz, H$_3$), 3.55 (dd, 1H, $^3J_{2,1}$=7.8 Hz, $^3J_{2,3}$=9.9 Hz, H$_2$), 2.93 (t, 1H, $^4J_{1''',1'}$=2.5 Hz, H$_{1'''}$)
$^{13}$C NMR (D$_2$O, 75 MHz) δ 101.13 (C$_1$), 78.99 (C$_{1''}$), 76.30 (C$_{1'''}$), 75.26 (C$_4$), 72.75 (C$_3$), 70.55 (C$_2$), 68.60 (C$_5$), 60.95 (C$_6$), 56.51 (C$_{1'}$)

Compound 8: 1,2,3,4-tetra-O-acetyl-L-rhamnopyranose of formula

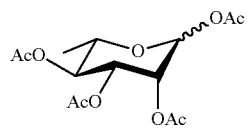

L-Rhamnose (109.0 mmol, 20.0 g) and acetic anhydride (0.85 mol, 80 ml) are dissolved in pyridine (0.99 mol, 80 ml). The reaction medium is stirred for 15 hours at room temperature. The solvent is evaporated under reduced pressure. The residue obtained is dissolved in 250 ml of ethyl acetate and washed with 2×100 ml of distilled water, 2×100 ml of saturated NaHCO$_3$ solution and 1×100 ml of saturated NaCl solution. The organic phase is dried over MgSO$_4$ and then filtered through sintered glass. The solvents are evaporated under reduced pressure and then coevaporated with 5×100 ml of toluene. The syrup obtained is dried in a desiccator overnight. Compound 8 is thus obtained in an a/β mixture (86:14) and with a yield of 98% (35.1 g).

Appearance: colorless syrup
M: 328.31 g·mol$^{-1}$
Empirical formula: $C_{15}H_{20}O_8$
Rf: 0.58 (cyclohexane/AcOEt: 50:50)
ESI-MS (M+Na$^+$): 355
FT-IR (ATR in cm$^{-1}$) 2956 (uC—H), 1744 (uC=O), 1368 (uC—O), 1209 (uC—O)
$^1$H NMR (CDCl$_3$, 300 MHz) α diastereoisomer: δ 5.96 (d, 1H, $^3J_{1,2}$=1.9 Hz, H$_1$), 5.27 (dd, 1H, $^3J_{3,2}$=3.5 Hz, $^3J_{3,4}$=10.0 Hz, H$_3$), 5.20 (dd, 1H, $^3J_{2,3}$=3.5 Hz, $^3J_{2,1}$=1.9 Hz, H$_2$), 5.06 (dd, 1H, $^3J_{4,3}$=10.0 Hz, $^3J_{4,5}$=10.0 Hz, H$_4$), 3.89 (dd, 1H, $^3J_{5,4}$=10.0 Hz, $^3J_{5,6}$=6.3 Hz, H$_5$), 2.11-1.94 (4s, 12H, CH$_3$CO$_2$), 1.18 (d, 3H, $^3J_{6,5}$=6.3 Hz, H$_6$)
$^{13}$C NMR (CDCl$_3$, 75 MHz) α diastereoisomer: δ 170.00-168.30 (CH$_3$CO$_2$), 90.63 (C$_1$), 70.46 (C$_4$), 68.78 (C$_2$, C$_3$ or C$_5$), 68.70 (C$_2$, C$_3$ or C$_5$), 68.64 (C$_2$, C$_3$ or C$_5$), 20.85-20.62 (CH$_3$CO$_2$), 17.42 (C$_6$)

Compound 9: propargyl 2,3,4-tri-O-acetyl-α-L-rhamnopyranoside of formula

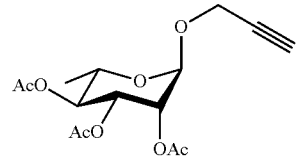

Compound 8 (11.14 mmol, 3.8 g) is placed under an inert atmosphere and dissolved in anhydrous dichloromethane (0.78 mol, 50 ml). Propargylic alcohol (13.72 mmol, 0.81 ml) is added to the reaction medium as well as boron trifluoride diethyl etherate at 0° C. (45.74 mmol, 5.65 ml). The mixture is stirred for 15 hours at room temperature. Potassium carbonate (17.15 mmol, 2.37 g) is added and the mixture is stirred for 30 minutes. The reaction medium is filtered through sintered glass. The collected yellow filtrate is concentrated under reduced pressure, diluted with 100 ml of dichloromethane and washed with 2×100 ml of distilled water. The aqueous phases are combined and extracted with 2×50 ml of dichloromethane. The organic phases are combined and dried over MgSO$_4$. The solvents are evaporated under reduced pressure. A brown oil is collected, which is purified by automated flash chromatography (cyclohexane/AcOEt: 100:0 to 60:40 over 20 minutes). The solid is dried in a desiccator overnight. Compound 9 is thus obtained with a yield of 79% (2.88 g).

Appearance: white solid
M: 328.31 g·mol$^{-1}$
Empirical formula: $C_{15}H_{20}O_8$
Rf: 0.65 (cyclohexane/AcOEt: 50:50)
Mp: 69-70° C.
[α]$_D^{20}$: −84.6° (c=1, CHCl$_3$)
ESI-MS (M+Na$^+$): 351
FT-IR (ATR in cm$^{-1}$): 3293 (uC≡H), 2988-2941 (uC—H), 1742 (uC=O), 1220-1212 (uC—O), 1054 (uC—O)
$^1$H NMR (CDCl$_3$, 300 MHz) δ 5.33 (dd, 1H, $^3J_{3,2}$=3.9 Hz, $^3J_{3,4}$=9.7 Hz, H$_3$), 5.18 (dd, 1H, $^3J_{2,3}$=3.9 Hz, $^3J_{2,1}$=1.0 Hz, H$_2$), 4.99 (t, 1H, $^3J_{4,3}$=9.7 Hz, H$_4$), 4.86 (dd, 1H, $^3J_{1,2}$=1.0 Hz, H$_1$), 4.18 (d, 2H, $^4J_{1',1'''}$=2.4 Hz, H$_{1'}$), 3.82 (dq, 1H, $^3J_{5,4}$=9.7 Hz, $^3J_{5,6}$=6.3 Hz, H$_5$), 2.43 (t, 1H, $^4J_{1''',1'}$=2.4 Hz, H$_{1'''}$), 2.07-1.90 (3s, 9H, CH$_3$CO$_2$), 1.15 (d, 3H, $^3J_{6,5}$=6.3 Hz, H$_6$)

$^{13}$C NMR (CDCl$_3$, 75 MHz) δ 170.02-169.97 (CH$_3$CO$_2$), 96.11 (C$_1$), 78.27 (C$_{1''}$), 75.35 (C$_{1'''}$), 70.95 (C$_4$), 69.66 (C$_2$), 69.01 (C$_3$), 66.92 (C$_5$), 20.92-20.73 (CH$_3$CO$_2$), 17.32 (C$_6$)

Compound 10: propargyl α-L-rhamnopyranoside of formula

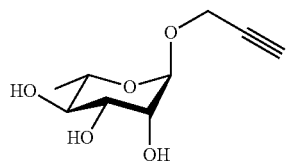

Compound 9 (16.5 mmol, 5.41 g) is dissolved in methanol (2.47 mol, 100 ml). A solution of sodium (10.0 mmol, 230 mg) in methanol (2.47 mol, 100 ml) is then added to the reaction medium. The solution is stirred for 15 hours at room temperature. An ion-exchange resin (IR-120 [H$^+$]) is added to a pH of 5-6. The mixture is filtered through sintered glass and the resin is washed with methanol. The solvents are evaporated under reduced pressure and the residue obtained is dried in a desiccator overnight. Compound 10 is obtained with a yield of 90% (3.0 g).

Appearance: white solid
M: 202.20 g·mol$^{-1}$
Empirical formula: C$_9$H$_{14}$O$_5$
Rf: 0.77 (CH$_2$Cl$_2$/MeOH: 80:20)
Mp: 105-107° C.
[α]$_D^{20}$: −23.1° (c=0.25, H$_2$O)
ESI-MS (M+Na$^+$): 225
FT-IR (ATR in cm$^{-1}$): 3543-3336 (uO—H), 3283 (uC≡H), 2946-2909 (uC—H), 2119 (uC≡C), 1446-1228 (uO—H), 1129-1048 (uC—O)

$^1$H NMR (D$_2$O, 300 MHz) δ 4.98 (d, 1H, $^3J_{1,2}$=1.5 Hz, H$_1$), 4.37 (dd, 1H, $^2J_{1'a,1'b}$=16.1 Hz, $^4J_{1'a,1'b}$=2.4 Hz, H$_{1'a}$), 4.31 (dd, 1H, $^2J_{1'b,1'a}$=16.1 Hz, $^4J_{1'b,1'''}$=2.4 Hz, H$_{1'b}$), 3.96 (dd, 1H, $^3J_{2,1}$=1.5 Hz, $^3J_{2,3}$=3.4 Hz, H$_2$), 3.77 (dd, 1H, $^3J_{3,2}$=3.4 Hz, $^3J_{3,4}$=9.6 Hz, H$_3$), 3.74 (dd, 1H, $^3J_{5,4}$=9.6 Hz, $^3J_{5,6}$=6.3 Hz, H$_5$), 3.47 (dd, 1H, $^3J_{4,3}$=9.6 Hz, $^3J_{4,5}$=9.6 Hz, H$_4$), 2.94 (t, 1H, $^4J_{1''',1'}$=2.4 Hz, H$_{1'''}$), 1.31 (d, 3H, $^3J_{6,5}$=6.3 Hz, H$_6$)

$^{13}$C NMR (D$_2$O, 75 MHz) δ 99.82 (C$_1$), 79.79 (C$_{1''}$), 77.09 (C$_{1'''}$), 72.85 (C$_4$), 71.10 (C$_2$), 70.94 (C$_3$), 70.02 (C$_5$), 55.64 (C$_{1'}$), 17.47 (C$_6$)

Compound 17: S-(2,3,4-tri-O-acetyl-α-L-rhamnopyranosyl)thiouronium of formula

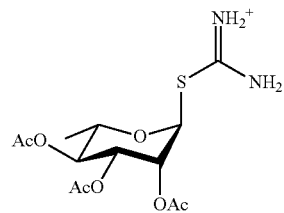

Compound 8 (5.12 mmol, 1.68 g) and thiourea (5.64 mmol, 0.43 g) are placed under an inert atmosphere and dissolved in anhydrous acetonitrile (0.19 mol, 10 ml). BF$_3$·Et$_2$O (10.76 mmol, 1.33 ml) is added to the reaction medium. The solution is refluxed for 30 minutes. The reaction medium is cooled to room temperature and pyridine is added (10.76 mmol, 0.90 ml). The solvents are evaporated under vacuum. The syrup obtained is diluted in 15 ml of isopropanol and the mixture is stirred rapidly at room temperature to crystallize the pyridinium-boron complex. The solid is filtered through sintered glass and the filtrate concentrated under reduced pressure. The residue obtained is dissolved in 15 ml of ethanol and the mixture is stirred rapidly at room temperature. The solid obtained is filtered through sintered glass, washed with ethanol and dried in a desiccator overnight. It consists of 80% by mass of compound 17 and 20% by mass of boron trifluoride-pyridinium salt. The yield is 85% (1.52 g).

Appearance: white solid
M: 349.38 g·mol$^{-1}$
Empirical formula: C$_{13}$H$_{21}$N$_2$O$_7$S
ESI-MS (M+Na$^+$): 371
FT-IR (ATR in cm$^{-1}$) 3389-3235 (uN—H), 1734 (uC=O), 1659 (uN—H), 1242-1066 (uC—O)

$^1$H NMR (C$_2$D$_6$SO, 300 MHz) δ 9.31 (s, 2H, NH$_2$), 9.25 (s, 2H, NH$_2$), 6.21 (d, 1H, $^3J_{1,2}$=1.2 Hz, H$_1$), 5.37 (dd, 1H, $^3J_{2,1}$=1.6 Hz, $^3J_{2,3}$=2.9 Hz, H$_2$), 4.99 (m, 2H, H$_3$ and H$_4$), 4.51 (m, 1H, H$_5$), 2.14-1.96 (3s, 9H, CH$_3$CO$_2$), 1.19 (d, 3H, $^3J_{6,5}$=6.2 Hz, H$_{6b}$)

$^{13}$C NMR (C$_2$D$_6$SO, 75 MHz) δ 169.72-169.36 (CH$_3$CO$_2$), 165.15 (SC(NH$_2$)$_2$), 81.67 (C$_1$), 69.59 (C$_3$ or C$_4$), 69.12 (C$_2$ and C$_5$), 68.43 (C$_3$ or C$_4$), 20.47-20.37 (CH$_3$CO$_2$), 17.11 (C$_6$)

Compound 18: propargyl 2,3,4-tri-O-acetyl-1-thio-α-L-rhamnopyranoside of formula

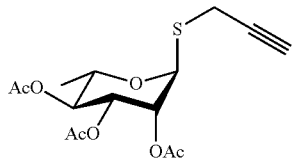

Compound 17 (3.22 mmol, 1.12 g) is placed under an inert atmosphere and dissolved in anhydrous acetonitrile (38.30 mmol, 20 ml). Triethylamine (9.97 mmol, 1.39 ml) is added followed by 80% propargyl bromide in toluene (3.54 mmol, 0.39 ml). The reaction medium is stirred for 1 hour at room temperature. The solvent is evaporated under vacuum and the syrup obtained is diluted in 30 ml of toluene. The organic phase is washed with 3×30 ml of distilled water. The aqueous phases are combined and extracted with 50 ml of toluene. The organic phases are combined and dried over MgSO$_4$. The solvent is evaporated under reduced pressure. The obtained yellowish syrup is purified by conventional chromatography on silica gel with an AcOEt/cyclohexane (20:80 to 40:60) elution gradient. The solid is dried in a desiccator overnight. Compound 18 is obtained with a yield of 73% (0.81 g).

Appearance: colorless syrup
M: 344.38 g·mol$^{-1}$
Empirical formula: C$_{15}$H$_{20}$O$_7$S
Rf: 0.28 (cyclohexane/AcOEt: 75:25)
[α]$_D^{20}$: −161.8° (c=1, CHCl$_3$)
ESI-MS (M+Na$^+$): 367

FT-IR (ATR in cm$^{-1}$): 3293 (u$C\equiv H$), 2985 (uC—H), 1742-1939 (u$C=O$), 1213-1039 (uC—O)

$^1$H NMR (CDCl$_3$, 300 MHz) δ 5.39 (d, 1H, $^3J_{1,2}$=1.3 Hz, H$_1$), 5.37 (dd, 1H, $^3J_{2,3}$=3.2 Hz, $^3J_{2,1}$=1.3 Hz, H$_2$), 5.18 (dd, 1H, $^3J_{3,2}$=3.2 Hz, $^3J_{3,4}$=10.0 Hz, H$_3$), 5.10 (dd, 1H, $^3J_{4,3}$=10.0 Hz, $^3J_{4,5}$=9.2 Hz, H$_4$), 4.18 (dq, 1H, $^3J_{5,4}$=9.2 Hz, $^3J_{5,6}$=6.2 Hz, H$_5$), 3.39 (dd, 1H, $^2J_{1'a,1'b}$=16.8 Hz, $^4J_{1'a,1'''}$=2.6 Hz, H$_{1'a}$), 3.22 (dd, 1H, $^2J_{1'b,1'a}$=16.8 Hz, $^4J_{1'b,1'''}$=2.6 Hz, H$_{1'b}$), 2.25 (t, 1H, $^4J_{1''',1'}$=2.6 Hz, H$_{1'''}$), 2.15-1.96 (3s, 9H, CH$_3$CO$_2$), 1.23 (d, 3H, $^3J_{6,5}$=6.2 Hz, H$_6$)

$^{13}$C NMR (CDCl$_3$, 75 MHz) δ 169.86-169.79 (CH$_3\underline{C}$O$_2$), 81.35 (C$_1$), 78.80 (C$_{1''}$), 71.92 (C$_{1'''}$), 71.06 (C$_4$), 70.79 (C$_2$), 69.54 (C$_3$), 67.45 (C$_5$), 20.87-20.61 ($\underline{C}$H$_3$CO$_2$), 18.24 (C$_{1'}$), 17.31 (C$_6$)

Compound 19: propargyl
1-thio-α-L-rhamnopyranoside of formula

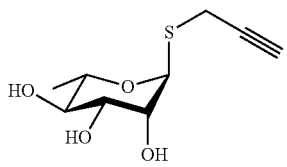

Compound 18 (3.48 mmol, 1.20 g) is dissolved in methanol (1.23 mol, 50 ml). A solution of sodium (5.0 mmol, 115 mg) in methanol (1.23 mol, 50 ml) is added to the reaction medium. The mixture is stirred for 15 hours at room temperature. Ion-exchange resin IR-120 [H$^+$] is added to a pH of 5-6. The reaction medium is filtered through sintered glass and the resin is washed with methanol. The solvent is evaporated under reduced pressure. The syrup obtained is dried in a desiccator overnight. Compound 19 is thus obtained with a yield of 88% (0.67 g).

Appearance: yellowish syrup
M: 218.27 g·mol$^{-1}$
Empirical formula: C$_9$H$_{14}$O$_4$S
Rf: 0.70 (CH$_2$Cl$_2$/MeOH: 75:25)
[α]$_D^{20}$: −298.4° (c=1, MeOH)
ESI-MS (M+Na$^+$): 241
FT-IR (ATR in cm$^{-1}$): 3385 (uO—H), 3288 (u$C\equiv H$), 2976-2933 (uC—H), 1058 (uC—O)

$^1$H NMR (D$_2$O, 300 MHz) δ 5.42 (s, 1H, H$_1$), 4.05 (dd, 1H, $^3J_{2,3}$=3.5 Hz, $^3J_{2,1}$=1.5 Hz, H$_2$), 4.00 (dq, 1H, $^3J_{5,4}$=3.4 Hz, $^3J_{5,6}$=6.3 Hz, H$_5$), 3.71 (dd, 1H, $^3J_{3,2}$=3.5 Hz, $^3J_{3,4}$=9.7 Hz, H$_3$), 3.47 (dd, 1H, $^3J_{4,3}$=9.7 Hz, $^3J_{4,5}$=3.4 Hz, H$_4$), 3.45 (dd, 1H, $^2J_{1'a,1'b}$=17.1 Hz, $^4J_{1'a,1'''}$=2.6 Hz, H$_{1'a}$), 3.34 (dd, 1H, $^2J_{1'b,1'a}$=17.1 Hz, $^4J_{1'b,1'''}$=2.6 Hz, H$_{1'b}$), 2.67 (t, 1H, $^4J_{1''',1'}$=2.6 Hz, H$_{1'''}$), 1.29 (d, 3H, $^3J_{6,5}$=6.3 Hz, H$_6$)

$^{13}$C NMR (D$_2$O, 75 MHz) δ 84.65 (C$_1$), 80.83 (C$_{1''}$), 73.06 (C$_{1'''}$), 72.95 (C$_4$), 72.13 (C$_2$), 71.62 (C$_3$), 70.13 (C$_5$), 18.51 (C$_{1'}$), 17.33 (C$_6$)

Compound 25: propargyl
2,3,6-tri-O-benzoyl-β-D-galactopyranoside of
formula

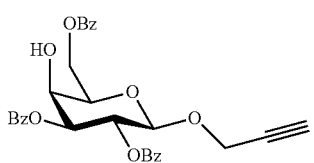

Compound 6 (0.92 mmol, 200 mg) is dissolved in pyridine (30.9 mmol, 2.5 ml) and cooled to 0° C. Benzoyl chloride (3.30 mmol, 0.38 ml) is then added and the solution is stirred for 15 hours at room temperature. The reaction is quenched by adding 4 ml of distilled water. The reaction medium is diluted with 20 ml of toluene and then washed successively with 20 ml of saturated NaHCO$_3$ solution, 20 ml of 1 M HCl solution and finally 20 ml of distilled water. The organic phase is dried over MgSO$_4$ and the solvents are evaporated under reduced pressure. The residue is purified by means of automated flash chromatography (cyclohexane/AcOEt: 100:0 to 80:20 over 30 minutes). The solid is dried in a desiccator overnight. Compound 25 is obtained with a yield of 70% (342 mg).

Appearance: white solid
M: 530.52 g·mol$^{-1}$
Empirical formula: C$_{30}$H$_{26}$O$_9$
Rf: 0.71 (cyclohexane/AcOEt: 50:50)
Mp: 78-79° C.
[α]$_D^{20}$: 25.0° (c=1, CHCl$_3$)
ESI-MS (M+Na$^+$): 553
FT-IR (ATR in cm$^{-1}$): 3458 (uO—H), 2971-2927 (uC—H), 1722-1704 (u$C=O$), 1318-1261 (uC—O), 1111-1072 (uC—O)

$^1$H NMR (CDCl$_3$, 300 MHz) δ 8.05-7.96 (m, 6H, CH=CH), 7.60-7.30 (m, 9H, CH=CH), 5.82 (dd, 1H, $^3J_{2,1}$=8.0 Hz, $^3J_{2,3}$=10.3 Hz, H$_2$), 5.40 (dd, 1H, $^3J_{3,2}$=10.3 Hz, $^3J_{3,4}$=3.2 Hz, H$_3$), 5.04 (d, 1H, $^3J_{1,2}$=8.0 Hz, H$_1$), 4.70 (dd, 1H, $^2J_{6a,6b}$=11.4 Hz, $^3J_{6a,5}$=6.4 Hz, H$_{6a}$), 4.70 (dd, 1H, $^2J_{6b,6a}$=11.4 Hz, $^3J_{6b,5}$=6.4 Hz, H$_{6b}$), 4.47 (dd, 1H, $^2J_{1'a,1'b}$=16.0 Hz, $^4J_{1'a,1'''}$=2.3 Hz, H$_{1'a}$), 4.41 (d, 1H, $^3J_{4,3}$=3.2 Hz, H$_4$), 4.37 (dd, 1H, $^2J_{1'b,1'a}$=16.0 Hz, $^4J_{1'b,1'''}$=2.3 Hz, H$_{1'b}$), 4.13 (t, 1H, $^3J_{5,6}$=6.4 Hz, H$_5$), 2.95 (s, 1H, OH), 2.38 (t, 1H, $^4J_{1''',1'}$=2.3 Hz, H$_{1'''}$)

$^{13}$C NMR (CDCl$_3$, 75 MHz) δ 166.57-165.59 (PhCO$_2$), 133.56-133.21 (CH=CH), 129.98-128.36 (CH=CH), 98.83 (C$_1$), 78.44 (C$_{1''}$), 75.44 (C$_{1'''}$), 74.32 (C$_3$), 72.70 (C$_5$), 69.40 (C$_2$), 67.35 (C$_4$), 62.96 (C$_6$), 55.87 (C$_{1'}$)

Compound 27: propargyl 4-S-(2,3,4-tri-O-acetyl-α-L-rhamnopyranosyl)-2,3,6-tri-O-benzoyl-4 thio-β-D-glucopyranoside of formula

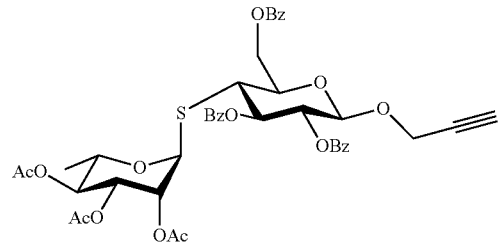

Compound 25 (1.22 mmol, 650 mg) is placed under an inert atmosphere and dissolved in anhydrous dichloromethane (0.14 mol, 9 ml). The reaction medium is placed at −20° C. and pyridine (9.8 mmol, 0.80 ml) is added followed by the addition of Tf$_2$O (2.5 mmol, 0.42 ml). The mixture is stirred for 2 hours while rising from −20° C. to 10° C. The solution is diluted with 20 ml of dichloromethane and is washed successively with 30 ml of 1 M HCl solution, 30 ml of saturated NaHCO$_3$ solution and 30 ml of saturated NaCl solution. The organic phase is dried over MgSO$_4$. A yellow syrup is directly obtained and placed under an inert atmosphere. Anhydrous acetonitrile (0.19 mol, 10 ml), triethylamine (4.4 mmol, 0.60 ml) and finally compound 17 (1.47 mmol, 647 mg) are added. The reaction medium is stirred for 2 hours at room temperature. The solvent is evaporated under reduced pressure and the residue obtained is diluted with 30 ml of toluene. The organic phase is washed with 2×30 ml of distilled water. The aqueous phases are combined and extracted with 2×30 ml of toluene. The organic phases are combined and dried over MgSO$_4$. The solvent is evaporated under reduced pressure. The syrup is purified by means of automated flash chromatography (cyclohexane/AcOEt: 100:0 to 75:25 over 20 minutes). The residue is dried in a desiccator overnight. Compound 27 is obtained with a yield of 60% (599 mg).

Appearance: white solid
M: 818.84 g·mol$^{-1}$
Empirical formula: $C_{42}H_{42}O_{15}S$
Rf: 0.61 (cyclohexane/AcOEt: 50:50)
Mp: 84-96° C.
$[\alpha]_D^{20}$ −22.8° (c=1, CHCl$_3$)
HRMS: 841.2150 (841.2142 calculated for $C_{42}H_{42}O_{15}SNa$)
FT-IR (ATR in cm$^{-1}$): 3286 (uC═H), 2972-2927 (uC—H), 1722-1704 (uC═O), 1318-1261 (uC—O), 1139-1028 (uC—O), 718 (uC—O)
$^1$H NMR (CDCl$_3$, 600 MHz): 8.08 (m, 2H, CH═CH), 7.95 (m, 4H, CH═CH), 7.60 (m, 1H, CH═CH), 7.49 (m, 4H, CH═CH), 7.36 (m, 4H, CH═CH), 5.66 (dd, 1H, $^3J_{3,2}$=9.5 Hz, $^3J_{3,4}$=11.1 Hz, H$_{Glc3}$), 5.46 (dd, 1H, $^3J_{2,1}$=8.0 Hz, $^3J_{2,3}$=9.5 Hz, H$_{Glc2}$), 5.45 (d, 1H, $^3J_{1,2}$=1.3 Hz, H$_{Rha1}$), 5.24 (dd, 1H, $^3J_{2,1}$=1.3 Hz, $^3J_{2,3}$=2.9 Hz, H$_{Rha2}$), 5.03 (d, 1H, $^3J_{1,2}$=8.0 Hz, H$_{Glc1}$), 4.96 (dd, 1H, $^3J_{3,4}$=10.0 Hz, $^3J_{3,2}$=2.9 Hz, H$_{Rha3}$), 4.95 (d, 1H, J=7.9 Hz, H$_{Rha4}$), 4.92 (dd, 1H, $^2J_{6a,6b}$=12.1 Hz, $^3J_{6a,5}$=2.3 Hz, H$_{Glc6a}$), 4.65 (dd, 1H, $^2J_{6b,6a}$=12.1 Hz, $^3J_{6b,5}$=4.4 Hz, H$_{Glc6b}$), 4.40 (dd, 1H, $^2J_{1'a,1'b}$=16.0 Hz, $^4J_{1'a,1'''}$=2.4 Hz, H$_{Glc1'a}$), 4.33 (dd, 1H, $^2J_{1'b,1'a}$=16.0 Hz, $^4J_{1'b,1'''}$=2.4 Hz, H$_{Glc1'b}$), 4.07 (ddd, 1H, $^3J_{5,4}$=11.1 Hz, $^3J_{5,6a}$=2.3 Hz, $^3J_{5,6b}$=4.4 Hz, H$_{Glc5}$), 3.92 (dq, 1H, $^3J_{5,4}$=2.0 Hz, $^3J_{5,6}$=6.2 Hz, H$_{Rha5}$), 3.36 (t, 1H, $^3J_{4,3}$=11.1 Hz, $^3J_{4,5}$=11.1 Hz, H$_{Glc4}$), 2.39 (t, 1H, $^4J_{1''',1'}$=2.4 Hz, H$_{Glc1'''}$), 1.99-1.89 (3s, 9H, CH$_3$CO$_2$), 0.96 (d, 3H, $^3J_{6,5}$=6.2 Hz H$_{Rha6}$)
$^{13}$C NMR (CDCl$_3$, 150 MHz): 169.66-169.49 (CH$_3$CO$_2$), 165.76-165.23 (PhCO$_2$), 133.22-133.16 (CH═CH), 129.84-128.23 (CH═CH), 98.04 (C$_{Glc1}$), 81.12 (C$_{Rha1}$), 78.09 (C$_{Glc1''}$), 75.66 (C$_{Glc1'''}$), 74.64 (C$_{Glc5}$), 72.49 (C$_{Glc2}$), 71.18 (C$_{Glc3}$), 70.84 (C$_{Rha2}$), 70.53 (C$_{Rha3}$ or C$_{Rha4}$), 69.01 (C$_{Rha3}$ or C$_{Rha4}$), 67.77 (C$_{Rha5}$), 63.51 (C$_{Glc6}$), 55.72 (C$_{Glc1'}$), 46.06 (C$_{Glc4}$), 20.55-20.49 (CH$_3$CO$_2$), 17.02 (C$_{Rha6}$)

Compound 28: propargyl[1-thio-α-L-rhamnopyranosyl-(1→4)]-β-D-glucopyranoside of formula

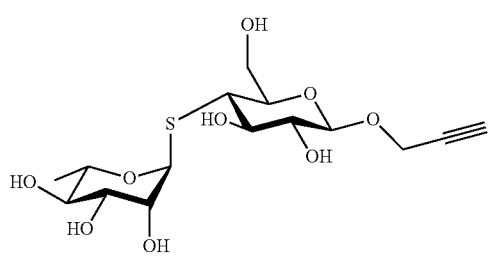

Compound 27 (0.60 mmol, 484 mg) is dissolved in methanol (0.37 mol, 15 ml). A solution of sodium (1.25 mmol, 29 mg) in methanol (0.25 mol, 10 ml) is added to the reaction medium. The solution is stirred for 15 hours at room temperature. Acid resin (IR-120 [H$^+$]) is added to a pH of 5-6. The mixture is filtered through sintered glass and the resin is washed with methanol. The solvent is evaporated under vacuum and the residue is purified by means of automated flash chromatography (CH$_2$Cl$_2$/MeOH: 100:0 to 75:25 over 30 minutes). The solid obtained is dried in a desiccator overnight. Compound 28 is obtained with a yield of 88% (197 mg).

Appearance: white solid
M: 380.41 g·mol$^{-1}$
Empirical formula: $C_{15}H_{24}O_9S$
Rf: 0.48 (CH$_2$Cl$_2$/MeOH: 75:25)
Mp: 47-69° C.
$[\alpha]_D^{20}$: −166.6° (c=1, MeOH)
HRMS: 403.1031 (403.1039 calculated for $C_{15}H_{24}O_9SNa$)
FT-IR (ATR in cm$^{-1}$): 3398 (uO—H), 2972-2900 (uC—H), 1056 (uC—O)
$^1$H NMR (CDCl$_3$, 600 MHz): 5.31 (d, 1H, $^3J_{1,2}$=1.2 Hz, H$_{Rha1}$), 4.63 (d, 1H, $^3J_{1,2}$=8.1 Hz, H$_{Glc1}$), 4.50 (dd, 1H, $^2J_{1'a,1'b}$=15.9 Hz, $^4J_{1'a,1'''}$=2.3 Hz, H$_{Glc1'a}$), 4.46 (dd, 1H, $^2J_{1'b,1'a}$=15.9 Hz, $^4J_{1'b,1'''}$=2.3 Hz, H$_{Glc1'b}$), 4.13 (dq, 1H, $^3J_{5,4}$=9.6 Hz, $^3J_{5,6}$=6.3 Hz, H$_{Rha5}$), 4.11 (dd, 1H, $^3J_{2,1}$=1.7 Hz, $^3J_{2,3}$=3.3 Hz, H$_{Rha2}$), 4.08 (dd, 1H, $^2J_{6a,6b}$=12.2 Hz, $^3J_{6a,5}$=2.0 Hz, H$_{Glc6a}$), 3.90 (dd, 1H, $^2J_{6b,6a}$=12.2 Hz, $^3J_{6b,5}$=5.2 Hz, H$_{Glc6b}$), 3.72 (dd, 1H, $^3J_{3,4}$=9.6 Hz, $^3J_{3,2}$=3.3 Hz, H$_{Rha3}$), 3.69 (ddd, 1H, $^3J_{5,4}$=10.9 Hz, $^3J_{5,6a}$=2.0 Hz, $^3J_{5,6b}$=5.2 Hz, H$_{Glc5}$), 3.61 (dd, 1H, $^3J_{3,2}$=9.1 Hz, $^3J_{3,4}$=10.9 Hz, H$_{Glc3}$), 3.49 (t, 1H, $^3J_{4,3}$=9.6 Hz, $^3J_{4,5}$=9.6 Hz, H$_{Rha4}$), 3.34 (t, 1H, $^3J_{2,3}$=8.5 Hz, $^3J_{2,1}$=8.5 Hz, H$_{Glc2}$), 2.93 (t, 1H, $^4J_{1''',1'}$=2.3 Hz, H$_{Glc1'''}$), 2.78 (t, 1H, $^3J_{4,3}$=10.9 Hz, $^3J_{4,5}$=10.9 Hz, H$_{Glc4}$), 1.30 (d, 3H, $^3J_{6,5}$=6.3 Hz H$_{Rha6}$)
$^{13}$C NMR (CDCl$_3$, 150 MHz): 100.38 (C$_{Glc1}$), 83.66 (C$_{Rha1}$), 78.93 (C$_{Glc1''}$), 76.49 (C$_{Glc1'''}$), 76.43 (C$_{Glc5}$), 74.16 (C$_{Glc2}$), 72.52 (C$_{Glc3}$, C$_{Rha2}$ or C$_{Rha4}$), 72.28 (C$_{Glc3}$, C$_{Rha2}$ or C$_{Rha4}$), 72.12 (C$_{Glc3}$, C$_{Rha2}$ or C$_{Rha4}$), 70.82 (C$_{Rha3}$), 69.68 (C$_{Rha5}$), 61.46 (C$_{Glc6}$), 56.54 (C$_{Glc1'}$), 48.02 (C$_{Glc4}$), 16.60 (C$_{Rha6}$)

Compound 54: propargyl 3,6-di-O-pivaloyl-β-D-glucopyranoside of formula

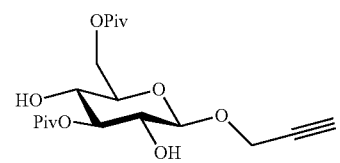

A solution of compound 3 (4.58 mmol, 1 g) in pyridine (98.9 mmol, 8 ml) and is placed at 0° C. Pivaloyl chloride (11.45 mmol, 1.41 ml) is then added dropwise. The reaction medium is stirred for 2.5 hours at 0° C. The solvent is evaporated under reduced pressure and the residue obtained is dissolved in 100 ml of ethyl acetate. The organic phase is washed successively with 100 ml of dilute HCl solution, 100 ml of saturated NaHCO$_3$ solution and finally 100 ml of saturated NaCl solution. The organic phase is dried over MgSO$_4$ and the solvent is evaporated under vacuum. The residue is purified by conventional chromatography on silica gel with an AcOEt/cyclohexane (10:90 to 40:60) elution gradient. The solid obtained is dried in a desiccator overnight. Compound 54 is obtained with a yield of 53% (0.94 g).

Appearance: Yellowish solid
M: 386.44 g·mol$^{-1}$
Empirical formula: $C_{19}H_{30}O_8$
Rf: 0.61 (cyclohexane/AcOEt: 50:50)
Mp: 65-66° C.
$[\alpha]_D^{20}$: −17.3° (c=0.5, CHCl$_3$)
ESI-MS (M+Na$^+$): 409
FT-IR (ATR in cm$^{-1}$): 3475 (uO—H), 3280 (uC≡H), 2972-2874 (uC—H), 1716 (uC=O), 1283-1036 (uC—O)
$^1$H NMR (CDCl$_3$, 300 MHz) δ 4.93 (t, 1H, $^3J_{3,2}$=9.2 Hz, $^3J_{3,4}$=9.2 Hz, H$_3$), 4.58 (d, 1H, $^3J_{1,2}$=7.8 Hz, H$_1$), 4.42 (dd, 1H, $^2J_{6a,6b}$=12.0 Hz, $^3J_{6a,5}$=2.4 Hz, H$_{6a}$), 4.40 (dd, 1H, $^2J_{1'a,1'b}$=15.8 Hz, $^4J_{1'a,1'''}$=2.4 Hz, H$_{1'a}$), 4.34 (dd, 1H, $^2J_{1'b,1'a}$=15.8 Hz, $^4J_{1'b,1'''}$=2.4 Hz, H$_{1'b}$), 4.27 (dd, 1H, $^2J_{6b-6a}$=12.0 Hz, $^3J_{6b,1}$=6.1 Hz, H$_{6b}$), 3.60 (ddd, 1H, $^3J_{5-6a}$=2.4 Hz, $^3J_{5-6b}$=6.1 Hz, $^3J_{5-4}$=9.8 Hz, H$_5$), 3.50 (dd, 1H, $^3J_{2,1}$=7.8 Hz, $^3J_{2,3}$=9.2 Hz, H$_2$), 3.47 (dd, 1H, $^3J_{4,3}$=9.2 Hz, $^3J_{4,5}$=9.8 Hz, H$_4$), 2.48 (t, 1H, $^4J_{1''',1}$=2.4 Hz, H$_{1'''}$), 1.23-1.20 (2s, 18H, (CH$_3$)$_3$CCO$_2$)
$^{13}$C NMR (CDCl$_3$, 75 MHz) δ 180.25-178.90 ((CH$_3$)$_3$C$\underline{C}$O$_2$), 100.31 (C$_1$), 78.46 (C$_{1''}$), 77.72 (C$_3$), 75.71 (C$_{1'''}$), 74.57 (C$_5$), 72.04 (C$_2$), 69.82 (C$_4$), 63.38 (C$_6$), 55.98 (C$_{1'}$), 39.15-39.00 ((CH$_3$)$_3$$\underline{C}$CO$_2$), 27.26-27.18 (($\underline{C}$H$_3$)$_3$CCO$_2$)

Compound 55: propargyl[(2,3,4-tri-O-acetyl-α-L-rhamnopyranosyl)-(1→4)]-[(2,3,4-tri-O-acetyl-α-L-rhamnopyranosyl)-(1→2)]-3,6-di-O-pivaloyl-β-D-glucopyranoside of formula

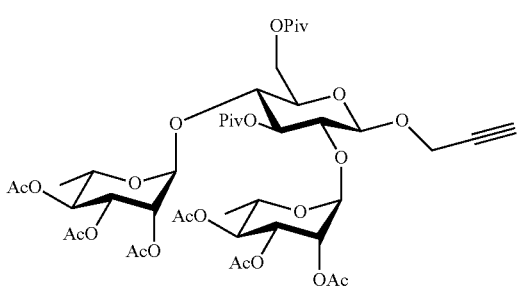

Compound 54 (1.56 mmol, 600 mg) is dissolved in 5 ml of anhydrous dichloromethane and then added to activated 4 Å molecular sieve placed under atmosphere. The reaction medium is placed at −78° C. and BF$_3$-Et$_2$O (7.02 mmol, 0.86 ml) is added. The solution is stirred for 1 hour at −78° C. Finally, compound 53 (4.68 mmol, 2.03 g) dissolved in 5 ml of anhydrous dichloromethane is added. The reaction mixture is stirred for 15 hours at room temperature. The molecular sieve is filtered through Celite and washed with ethyl acetate. The filtrate is concentrated under reduced pressure and the residue obtained is taken up in 20 ml of chloroform. The organic phase is washed with 20 ml of saturated NaHCO$_3$ solution and then 20 ml of saturated NaCl solution. It is then dried over MgSO$_4$ and the solvent is evaporated under vacuum. The obtained yellowish solid is purified by means of automated normal-phase flash chromatography (cyclohexane/AcOEt: 100:0 to 0:100 over 30 minutes) or automated reversed-phase flash chromatography (H$_2$O/MeOH: 70:30 to 0:100 over 20 minutes). The solid obtained is dried in a desiccator overnight. Compound 55 is isolated with a yield of 71% (1.03 g).

Appearance: white solid
M: 930.44 g·mol$^{-1}$
Empirical formula: $C_{43}H_{62}O_{22}$
Rf: 0.60 (cyclohexane/AcOEt: 50:50)
Mp: 82-86° C.
$[\alpha]_D^{20}$: −48.4° (c=1, CHCl$_3$)
HRMS: 953.3591 (953.3630 calculated for $C_{43}H_{62}O_{22}$Na)
FT-IR (ATR in cm$^{-1}$): 3445 (uO—H), 2977 (uC—H), 1745 (uC=O), 1220-1042 (uC—O)
$^1$H NMR (CDCl$_3$, 600 MHz): 5.26 (t, 1H, $^3J_{3,4}$=$^3J_{3,2}$=7.4 Hz, H$_{Glc3}$), 5.23 (dd, 1H, $^3J_{3,4}$=10.0 Hz, $^3J_{3,2}$=3.4 Hz, H$_{Rha3'}$), 5.19 (d, 1H, $^3J_{2,3}$=3.4 Hz, H$_{Rha2'}$), 5.18 (dd, 1H, $^3J_{3,4}$=10.0 Hz, $^3J_{3,2}$=3.2 Hz, H$_{Rha3}$), 5.05 (dd, 1H, $^3J_{2,1}$=1.6 Hz, $^3J_{2,3}$=3.2 Hz, H$_{Rha2}$), 5.04 (dd, 1H, $^3J_{4,3}$=10.0 Hz, $^3J_{4,5}$=10.0 Hz, H$_{Rha4}$ or H$_{Rha4'}$), 5.01 (dd, 1H, $^3J_{4,3}$=10.0 Hz, $^3J_{4,5}$=10.0 Hz, H$_{Rha4}$ or H$_{Rha4'}$), 4.87 (d, 1H, $^3J_{1,2}$=1.6 Hz, H$_{Rha1}$), 4.81 (s, 1H, H$_{Rha1'}$), 4.74 (d, 1H, $^3J_{1,2}$=7.0 Hz, H$_{Glc1}$), 4.48 (dd, 1H, $^2J_{6a,6b}$=12.1 Hz, $^3J_{6a,5}$=1.6 Hz, H$_{Glc6a}$), 4.36 (dd, 1H, $^2J_{1'a,1'b}$=16.0 Hz, $^4J_{1'a,1'''}$=2.3 Hz, H$_{Glc1'a}$), 4.33 (dd, 1H, $^2J_{1'b,1'a}$=16.0 Hz, $^4J_{1'b,1'''}$=2.3 Hz, H$_{Glc1'b}$), 4.26 (dd, 1H, $^2J_{6b,6a}$=12.1 Hz, $^3J_{6b,5}$=4.5 Hz, H$_{Glc6b}$), 4.21 (dq, 1H, $^3J_{5,4}$=10.0 Hz, $^3J_{5,6}$=6.3 Hz, H$_{Rha5}$ or H$_{Rha5'}$), 3.91 (dq, 1H, $^3J_{5,4}$=10.0 Hz, $^3J_{5,6}$=6.3 Hz, H$_{Rha5}$ or H$_{Rha5'}$), 3.78 (m, 2H, H$_{Glc4}$ and H$_{Glc5}$), 3.59 (t, 1H, $^3J_{2,3}$=7.4 Hz, $^3J_{2,1}$=7.4 Hz, H$_{Glc2}$), 2.49 (t, 1H, $^4J_{1''',1}$=2.3 Hz, H$_{Glc1'''}$), 2.11-1.94 (6s, 18H, CH$_3$CO$_2$), 1.22 (s, 9H, (CH$_3$)$_3$CCO$_2$), 1.19 (d, 3H, $^3J_{6,5}$=6.3 Hz, H$_{Rha6}$ or H$_{Rha6'}$), 1.17 (s, 9H, (CH$_3$)$_3$CCO$_2$), 1.15 (d, 3H, $^3J_{6,5}$=6.3 Hz H$_{Rha6}$ or H$_{Rha6'}$)
$^{13}$C NMR (CDCl$_3$, 150 MHz): 177.74-176.45 ((CH$_3$)$_3$C$\underline{C}$O$_2$), 170.02-169.53 (CH$_3$$\underline{C}$O$_2$), 98.11 (C$_{Rha1'}$), 98.16 (C$_{Glc1}$), 97.42 (C$_{Rha1}$), 78.02 (C$_{Glc1'''}$), 77.79 (C$_{Glc2}$), 76.56 (C$_{Glc4}$ or C$_{Glc5}$), 75.74 (C$_{Glc1''}$), 75.08 (C$_{Glc3}$), 72.32 (C$_{Glc4}$ or C$_{Glc5}$), 70.94 (C$_{Rha4}$ or C$_{Rha4'}$), 70.53 (C$_{Rha4}$ or C$_{Rha4'}$), 69.98 (C$_{Rha2}$ or C$_{Rha2'}$), 69.61 (C$_{Rha2}$ or C$_{Rha2'}$), 69.05 (C$_{Rha3}$ or C$_{Rha3'}$), 68.69 (C$_{Rha3}$ or C$_{Rha3'}$), 67.97 (C$_{Rha5}$ or C$_{Rha5'}$), 66.81 (C$_{Rha5}$ or C$_{Rha5'}$), 62.40 (C$_{Glc6}$), 55.51 (C$_{Glc1'}$), 38.88-38.81 ((CH$_3$)$_3$$\underline{C}$CO$_2$), 27.15-26.86 (($\underline{C}$H$_3$)$_3$CCO$_2$), 20.80-20.67 ($\underline{C}$H$_3$CO$_2$), 17.16-17.09 (C$_{Rha6}$ and C$_{Rha6'}$)

Compound 56: propargyl[(α-L-rhamnopyranosyl)-(1→4)]-[(α-L-rhamnopyranosyl)-(1→2)]-β-D-glucopyranoside of formula

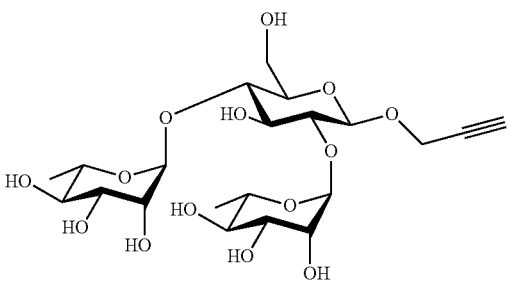

Compound 55 (0.81 mmol, 749 mg) is dissolved in methanol (0.61 mol, 25 ml). A solution of sodium (25 mmol, 575 mg) in methanol (0.61 mol, 25 ml) is added. The reaction mixture is stirred for 15 hours at room temperature. Acid resin (IR-120 [H$^+$]) is added to a pH of 5-6. The resin is filtered through sintered glass and washed with methanol. The solvent is evaporated under reduced pressure and the residue obtained is purified by means of automated reversed-phase flash chromatography (H₂O/MeOH: 100:0 to 0:100 over 20 minutes). The product is dried in a desiccator overnight. Compound 56 is isolated with a yield of 87% (360 mg).

Appearance: white solid
M: 510.49 g·mol$^{-1}$
Empirical formula: $C_{21}H_{34}O_{14}$
Rf: 0.17 (CH₂Cl₂/MeOH: 75:25)
Mp: 56-66° C.
$[\alpha]_D^{20}$: -98.7° (c=1, MeOH)
HRMS: 533.1857 (533.1846 calculated for $C_{21}H_{34}O_{14}Na$)
FT-IR (ATR in cm$^{-1}$): 3390 (uO—H), 2931 (uC—H), 1128-1041 (uC—O)
$^{1}$H NMR (CDCl₃, 600 MHz): 5.03 (d, 1H, $^{3}J_{1,2}$=1.5 Hz, H$_{Rha1}$), 4.85 (d, 1H, $^{3}J_{1,2}$=1.4 Hz, H$_{Rha1'}$), 4.71 (d, 1H, $^{3}J_{1,2}$=7.9 Hz, H$_{Glc1}$), 4.50 (dd, 1H, $^{2}J_{1'a,1'b}$=15.8 Hz, $^{4}J_{1'a,1'''}$=2.3 Hz, H$_{Glc1'a}$), 5.46 (dd, 1H, $^{2}J_{1'b,1'a}$=15.8 Hz, $^{4}J_{1'b,1'''}$=2.3 Hz, H$_{Glc1'b}$), 4.03 (m, 4H, H$_{Rha2}$, H$_{Rha2'}$, H$_{Rha5}$ and H$_{Rha5'}$), 3.89 (dd, 1H, $^{2}J_{6a,6b}$=12.4 Hz, $^{3}J_{6a,5}$=2.2 Hz, H$_{Glc6a}$), 3.77 (t, 1H, $^{3}J_{3,2}$=$^{3}J_{3,4}$=9.8 Hz, H$_{Rha3}$), 3.76 (t, 1H, $^{3}J_{3,2}$=$^{3}J_{3,4}$=9.8 Hz, H$_{Rha3'}$), 3.74 (m, 2H, H$_{Glc3}$ and H$_{Glc6b}$), 3.59 (t, 1H, $^{3}J_{4,3}$=9.5 Hz, $^{3}J_{4,5}$=9.5 Hz, H$_{Glc4}$), 3.51 (ddd, 1H, $^{3}J_{5,4}$=9.5 Hz, $^{3}J_{5,6a}$=2.2 Hz, $^{3}J_{5,6b}$=4.6 Hz, H$_{Glc5}$), 3.47 (t, 1H, $^{3}J_{4,3}$=$^{3}J_{4,5}$=9.8 Hz, H$_{Rha4}$), 3.46 (t, 1H, $^{3}J_{4,3}$=$^{3}J_{4,3}$=9.8 Hz, H$_{Rha4'}$), 3.38 (dd, 1H, $^{3}J_{2,1}$=7.9 Hz, $^{3}J_{2,3}$=9.0 Hz, H$_{Glc2}$), 2.94 (t, 1H, $^{4}J_{1''',1'}$=2.3 Hz, H$_{Glc1'''}$), 1.29 (d, 3H, $^{3}J_{6,5}$=6.3 Hz, H$_{Rha6}$), 1.26 (d, 3H, $^{3}J_{6,5}$=6.3 Hz, H$_{Rha6'}$)
$^{13}$C NMR (CDCl₃, 150 MHz): 101.78 (C$_{Rha1}$), 101.02 (C$_{Rha1'}$), 99.34 (C$_{Glc1}$), 80.19 (C$_{Glc2}$), 78.84 (C$_{Glc1'''}$), 77.05 (C$_{Glc4}$), 76.59 (C$_{Glc1'''}$), 75.15 (C$_{Glc5}$), 74.93 (C$_{Glc3}$), 72.08 (C$_{Rha4}$ or C$_{Rha4'}$), 72.00 (C$_{Rha4}$ or C$_{Rha4'}$), 70.46 (C$_{Rha2}$, C$_{Rha2'}$, C$_{Rha3}$ or C$_{Rha3'}$), 70.33 (C$_{Rha2}$, C$_{Rha2'}$, C$_{Rha3}$ or C$_{Rha3'}$), 70.29 (C$_{Rha2}$, C$_{Rha2'}$, C$_{Rha3}$ or C$_{Rha3'}$), 70.27 (C$_{Rha2}$, C$_{Rha2'}$, C$_{Rha3}$ or C$_{Rha3'}$), 69.12 (C$_{Rha5}$ or C$_{Rha5'}$), 69.04 (C$_{Rha5}$ or C$_{Rha5'}$), 60.18 (C$_{Glc6}$), 56.62 (C$_{Glc1'}$), 16.76-16.57 (C$_{Rha6}$ and C$_{Rha6'}$)

Compound 66: 3-azidopropan-1-ol of formula

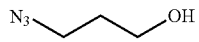

3-Chloropropan-1-ol (0.11 mol, 10 g) is dissolved in distilled water (0.81 mol, 45 ml). Sodium azide (0.21 mmol, 13.78 g) is added and the reaction medium is stirred for 15 hours at 80° C. The reaction medium is washed with 3×50 ml of diethyl ether. The organic phases are combined and dried over MgSO₄. Because the product is volatile, the solvent is evaporated under reduced pressure at mild temperature (15° C.). Compound 66 is obtained with a yield of 99% (11.0 g).

Appearance: colorless liquid
M: 101.11 g·mol$^{-1}$
Empirical formula: $C_3H_7N_3O$
Rf: 0.47 (cyclohexane/AcOEt: 50:50)
ESI-MS (M+Na$^{+}$): 124
FT-IR (ATR in cm$^{-1}$) 3332 (uO—H), 2946 (uC—H), 2883 (uC—H), 2089 (uN≡N), 1258 (uC—O), 1045 (uC—N)
$^{1}$H NMR (CDCl₃, 300 MHz) δ 3.60 (s, 1H, OH), 3.47 (t, 2H, $^{3}J$=6.4 Hz, CH₂OH), 3.21 (t, 2H, $^{3}J$=6.4 Hz, CH₂N₃), 1.61 (qt, 2H, $^{3}J$=6.4 Hz, $^{3}J$=6.4 Hz, CH₂C̲H₂CH₂) $^{13}$C NMR (CDCl₃, 75 MHz) δ 58.63 (CH₂OH), 47.74 (CH₂N₃), 30.94 (CH₂C̲H₂CH₂)

Compound 67: 3-azidopropyl p-toluenesulfonate of formula

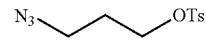

Compound 66 (0.11 mol, 11.5 g) is dissolved in dichloromethane (1.72 mol, 110 ml). DMAP (23.0 mmol, 2.78 g) is added, followed by triethylamine (0.17 mol, 23.8 ml). The reaction medium is placed at 0° C. A solution of tosyl chloride (0.17 mol, 32.41 g) in dichloromethane (0.94 mol, 60 ml) is added to the reaction. The reaction mixture is stirred for 15 hours while rising from 0° C. to room temperature. The reaction medium is diluted with 200 ml of dichloromethane and washed successively with 200 ml of saturated NaHCO₃ solution, 200 ml of 10% by volume HCl solution and 200 ml of saturated NaCl solution. The organic phase is dried over MgSO₄ and the solvents are evaporated under reduced pressure. The residue is purified by conventional chromatography on silica gel with cyclohexane/Et₂O (80:20 to 60:40) elution gradient. Compound 67 is obtained with a yield of 76% (21.4 g).

Appearance: colorless crystal
M: 255.29 g·mol$^{-1}$
Empirical formula: $C_{10}H_{23}N_3O_3S$
Rf: 0.57 (cyclohexane/Et₂O: 50/50)
Mp: 28-29° C.
ESI-MS (M+Na$^{+}$): 278
FT-IR (ATR in cm$^{-1}$) 2957 (uC—H), 2095 (uN≡N), 1598 (uC=N), 1356 (uSO₂), 1188 (uSO₂), 1172 (uC—O), 662 (uSO₂)
$^{1}$H NMR (CDCl₃, 300 MHz) δ 7.80 (d, 2H, $^{3}J$=8.0 Hz, CH=CH), 7.38 (d, 2H, $^{3}J$=8.0 Hz, CH=CH), 4.12 (t, 2H, $^{3}J$=6.3 Hz, CH₂OSO₂), 3.38 (t, 2H, $^{3}J$=6.3 Hz, CH₂N₃), 2.45 (s, 3H, CH₃), 1.89 (q', 2H, $^{3}J$=6.3 Hz, CH₂C̲H₂CH₂)
$^{13}$C NMR (CDCl₃, 75 MHz) δ 144.86 (CSO₃), 132.42 (C̲CH₃), 129.73 (CH=CH), 127.54 (CH=CH), 67.01 (CH₂OSO₂), 46.99 (CH₂N₃), 28.06 (CH₂C̲H₂CH₂), 21.24 (C̲CH₃)

Compound 75: 3-O-(3-azidopropyl)solanidine of formula

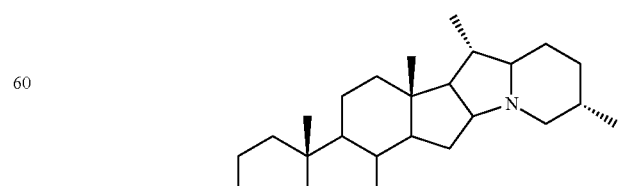

Solanidine (0.25 mmol, 100 mg) is placed under an inert atmosphere and dissolved in anhydrous THF (49.3 mmol, 4 ml). Ninety-five percent NaH (0.50 mmol, 13 mg) is then added and the reaction mixture is stirred at room temperature for 30 minutes. Compound 67 (1.26 mmol, 0.32 g) is then added and the solution is stirred at 60° C. for 24 hours. The solvents are evaporated under reduced pressure and then the residue is dissolved in chloroform and filtered through Celite. After concentration of the filtrate, the residue obtained is purified by CPC (conditions described above). A mixture of solanidine and compound 75 is isolated. Product 75 is recrystallized in acetonitrile with a yield of 71% (85 mg).

Appearance: colorless solid
M: 469.75 g·mol$^{-1}$
Empirical formula: $C_{30}H_{51}N_3O$
Rf: 0.59 (100% toluene)
Mp: 42-48° C.
$[\alpha]_D^{20}$: −14.4° (c=0.25, CHCl$_3$)
HRMS: 492.3919 (492.3930 calculated for $C_{30}H_{51}N_3ONa$)
FT-IR (ATR in cm$^{-1}$): 2991 ($u_{C-H}$), 2216 ($u_{N=N}$), 1648 ($u_{C=N}$), 1547 ($u_{C=C}$), 1026 ($u_{C-O}$)
$^1$H NMR (CDCl$_3$, 300 MHz) δ 5.34 (dd, 1H, $^3J_{6,7a}$=1.7 Hz, $^3J_{6,7b}$=3.3 Hz, H$_6$), 3.54 (t, 2H, $^3J_{3''',3''}$=6.2 Hz, H$_{3'''}$), 3.39 (t, 2H, $^3J_{3',3''}$=6.7 Hz, H$_{3'}$), 3.13 (m, 1H, H$_3$), 2.35 (ddd, 1H, $^2J_{4a,4b}$=13.2 Hz, $^3J_{4a,3}$=2.1 Hz, J=4.7 Hz, H$_{4a}$), 2.18 (dd, 1H, $^2J_{4b,4a}$=13.2 Hz, $^3J_{4b,3}$=2.1 Hz, H$_{4b}$), 2.04-1.76 (m, 4H), 1.82 (dt, 2H, $^3J_{3'',3'}$=6.7 Hz, $^3J_{3'',3'''}$=6.2 Hz, H$_{3''}$), 1.62-1.02 (m, 22H), 0.99 (s, 3H, H$_{19}$), 0.91 (d, 3H, $^3J_{21,20}$=6.5 Hz, H$_{21}$), 0.86 (d, 3H, $^3J_{27,25}$=6.6 Hz, H$_{27}$), 0.85 (d, 3H, $^3J_{26,25}$=6.6 Hz, H$_{26}$), 0.67 (s, 3H, H$_{18}$)
$^{13}$C NMR (CDCl$_3$, 75 MHz) δ 140.94 (C$_5$), 121.73 (C$_6$), 79.37 (C$_3$), 64.54 (C$_{3'}$), 56.89 (C$_{14}$), 56.31 (C$_{17}$), 50.32 (C$_9$), 48.68 (C$_{3'''}$), 42.44 (C$_{13}$), 39.91 (C$_{12}$), 39.64 (C$_{24}$), 39.21 (C$_4$), 37.35 (C$_1$), 36.99 (C$_{10}$), 36.33 (C$_{22}$), 35.92 (C$_{20}$), 32.06 (C$_7$), 32.01 (C$_8$), 29.73 (C$_{3''}$), 28.50 (C$_2$), 28.36 (C$_{16}$), 28.12 (C$_{25}$), 24.41 (C$_{15}$), 23.98 (C$_{23}$), 22.94 (C$_{27}$), 22.69 (C$_{26}$), 21.20 (C$_{11}$), 19.48 (C$_{19}$), 18.84 (C$_{21}$), 11.97 (C$_{18}$)

1-3. Preparation of the Compounds According to the Invention

Compound 100: 3-O-{3-[4-(β-D-glucopyranosyloxymethyl)-1,2,3-triazol-1-yl]propyl}solanidine of formula Compound 75 (0.08 mmol, 40 mg) and compound 3 (0.10 mmol, 22 mg) are dissolved in 3.75 ml of a mixture of 1,4-dioxane and H$_2$O (4:1 by volume). Copper(II) sulfate (0.12 mmol, 19 mg) and sodium ascorbate (0.23 mmol, 47 mg) are then added. The reaction medium is stirred at 80° C. for 24 hours. The mixture is filtered through Celite and the collected filtrate is concentrated under reduced pressure. The residue is purified by CPC. Compound 100 is obtained with a yield of 48% (27 mg).

Appearance: yellow oil
M: 698.93 g·mol$^{-1}$
Empirical formula: $C_{39}H_{62}N_4O_7$
Rf: 0.29 (CHCl$_3$/MeOH: 80:20)
$[\alpha]_D^{20}$: −19.2° (c=0.1, MeOH)
HRMS: 699.4722 (699.4697 calculated for $C_{39}H_{63}N_4O_7$)
FT-IR (ATR in cm$^{-1}$): 3393 (uO—H), 2925-2854-(uC—H), 1076-1036 (uC—O)
$^1$H NMR (pyridine-d$_5$, 600 MHz): 8.17 (s, 1H, H$_{Glc1'''}$), 5.38 (d, 1H, $^2J_{1'a,1'b}$=12.3 Hz, H$_{Glc1'a}$), 5.36 (S, 1H, H$_6$), 5.17 (d, 1H, $^2J_{1'b,1'a}$=12.3 Hz, H$_{Glc1'b}$), 5.07 (d, 1H, $^3J_{1,2}$=7.6 Hz, H$_{Glc1}$), 4.57 (dd, 1H, $^2J_{6a,6b}$=12.0 Hz, $^3J_{6a,5}$=2.4 Hz, H$_{Glc6a}$), 4.52 (t, 2H, J=9.8 Hz, H$_{3'''}$), 4.38 (dd, 1H, $^2J_{6b,6a}$=12.0 Hz, $^3J_{6b,5}$=5.3 Hz, H$_{Glc6b}$), 4.26 (m, $^2$H, H$_{Glc3}$ and H$_{Glc4}$), 4.09 (m, 1H, H$_{Glc2}$), 3.98 (m, 1H, H$_{Glc5}$), 3.60 (s, 1H, H$_{26a}$), 3.44-(m, 3H, H$_{3'}$ and H$_{16}$), 3.08 (m, 1H, H$_3$), 2.56-1.84-(m, 6H, H$_4$, H$_{3'''}$, H$_{22}$ and H$_{26b}$), 1.72-1.10 (m, 24H), 0.93 (s, 3H, H$_{19}$), 0.92 (d, 3H, $^3J_{21,20}$=13.1 Hz, H$_{21}$), 0.91 (m, 1H), 0.75 (d, 3H, $^3J_{27,26}$=13.1 Hz, H$_{27}$)
$^{13}$C NMR (pyridine-d$_5$, 150 MHz): 145.63 (C$_{Glc1''}$), 141.39 (C$_5$), 124.71 (C$_{Glc1'''}$), 121.68 (C$_6$), 104.46 (C$_{Glc1}$), 79.53 (C$_3$), 78.95 (C$_{Glc3}$, C$_{Glc4}$ or C$_{Glc5}$), 78.89 (C$_{Glc3}$, C$_{Glc4}$ or C$_{Glc5}$), 75.87 (C$_{22}$), 75.50 (C$_{Glc2}$), 72.00 (C$_{Glc3}$, C$_{Glc4}$ or C$_{Glc5}$), 70.86 (C$_{16}$), 64.56 (C$_{3'}$), 63.48 (C$_{Glc1'}$), 63.07 (C$_{Glc6}$), 61.16 (C$_{17}$), 59.08 (C$_{26}$), 57.94-(C$_{14}$), 50.44-(C$_9$), 47.82 (C$_{3'''}$), 40.91 (C$_{13}$), 40.54-(C$_{12}$), 39.76 (C$_4$), 37.60 (C$_1$), 37.50 (C$_{10}$), 36.90 (C$_{20}$), 32.54-(C$_{24}$), 31.79 (C$_{15}$), 31.56 (C$_{3''}$), 31.40 (C$_{25}$), 30.29 (C$_{23}$), 29.04-(C$_8$), 28.57 (C$_7$), 27.35 (C$_2$), 21.42 (C$_{11}$), 19.66 (C$_{19}$), 18.88 (C$_{27}$), 16.87 (C$_{18}$), 16.35 (C$_{21}$)

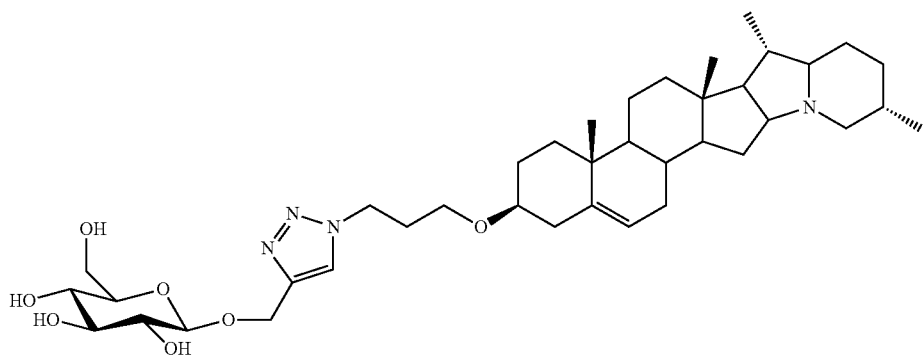

Compound 101: 3-O-{3-[4-(β-D-galactopyranosyloxymethyl)-1,2,3-triazol-1-yl]propyl}solanidine of formula

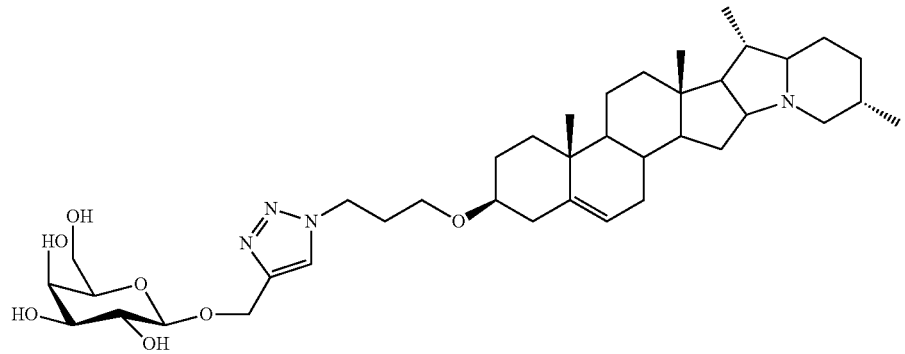

Compound 75 (0.08 mmol, 40 mg) and compound 6 (0.10 mmol, 22 mg) are dissolved in 3.75 ml of a mixture of 1,4-dioxane and H$_2$O (4:1 by volume). Copper(II) sulfate (0.12 mmol, 19 mg) and sodium ascorbate (0.23 mmol, 47 mg) are then added. The reaction medium is stirred at 80° C. for 24 hours. The mixture is filtered through Celite and the collected filtrate is concentrated under reduced pressure. The residue is purified by CPC. Compound 101 is obtained with a yield of 55% (31 mg).

Appearance: yellow oil
M: 698.93 g·mol$^{-1}$
Empirical formula: C$_{39}$H$_{62}$N$_4$O$_7$
Rf: 0.23 (CHCl$_3$/MeOH: 80:20)
[α]$_D^{20}$: −16.7° (c=0.1, MeOH)
HRMS: 699.4711 (699.4697 calculated for C$_{39}$H$_{63}$N$_4$O$_7$)
FT-IR (ATR in cm$^{-1}$): 3378 (uO—H), 2934-2866 (uC—H), 1092-1041 (uC—O)
$^1$H NMR (pyridine-d$_5$, 600 MHz): 8.11 (s, 1H, H$_{Gal1'''}$), 5.42 (d, J=5.8 Hz, 1H, H$_6$), 5.41 (d, 1H, $^2$J$_{1'a,1'b}$=12.3 Hz, H$_{Gal1'a}$), 5.19 (d, 1H, $^2$J$_{1'b,1'a}$=12.3 Hz, H$_{Gal1'b}$), 5.00 (d, 1H, $^3$J$_{1,2}$=7.7 Hz, H$_{Gal1}$), 4.58 (d, 1H, $^3$J$_{4,3}$=3.0 Hz, H$_{Gal4}$), 4.50 (m, 5H, H$_{3'''}$, H$_{Gal2}$, H$_{Gal6a}$ and H$_{Gal6b}$), 4.19 (dd, 1H, $^3$J$_{3,4}$=3.0 Hz, $^3$J$_{3,2}$=9.4 Hz, H$_{Gal3}$), 4.11 (t, 1H, J=5.9 Hz, H$_{Gal5}$), 3.43 (dq, 2H, J=6.0 Hz, J=9.7 Hz, H$_{3'}$), 3.17 (dq, 1H, J=11.3 Hz, J=6.6 Hz, H$_3$), 2.93 (dd, 1H, J=10.3 Hz, J=2.5 Hz, H$_{26a}$), 2.67 (m, 1H, H$_{16}$), 2.48 (dd, 1H, J=13.1 Hz, J=2.5 Hz, H$_{4a}$), 2.32 (t, 1H, J=11.3 Hz, H$_{4b}$), 2.12 (q$^t$, 2H, J=6.6 Hz, H$_{3''}$), 2.04-(m, 1H), 1.92 (m, 1H), 1.81-1.38 (m, 18H), 1.26 (q, 1H, J=13.0 Hz, H$_{23b}$), 1.14-(m, 3H), 1.03-0.93 (m, 3H), 0.99 (s, 3H, H$_{19}$), 0.98 (d, 3H, $^3$J$_{21,20}$=5.9 Hz, H$_{21}$), 0.96 (s, 3H, H$_{18}$), 0.84-(d, 3H, $^3$J$_{27,26}$=6.4 Hz, H$_{27}$), 0.82 (m, 1H, H$_{24}$)

$^{13}$C NMR (pyridine-d$_5$, 150 MHz): 145.78 (C$_{Gal1'''}$), 141.40 (C$_5$), 124.19 (C$_{Gal1''}$), 122.19 (C$_6$), 105.06 (C$_{Gal1}$), 79.64-(C$_3$), 77.55 (C$_{Gal5}$), 75.75 (C$_{Gal3}$), 75.13 (C$_{22}$), 72.90 (C$_{Gal2}$), 70.67 (C$_{Gal4}$), 69.62 (C$_{16}$), 64.62 (C$_{3'}$), 63.72 (C$_{17}$), 63.40 (C$_{Gal1'}$), 62.86 (C$_{Gal6}$), 60.64-(C$_{26}$), 58.14-(C$_{14}$), 50.87 (C$_9$), 47.85 (C$_{3'''}$), 40.94-(C$_{13}$), 40.45 (C$_{12}$), 39.92 (C$_4$), 37.76 (C$_1$), 37.55 (C$_{10}$), 37.28 (C$_{20}$), 34.00 (C$_{24}$), 32.77 (C$_8$), 32.32 (C$_7$), 31.90 (C$_{15}$), 31.70 (C$_{25}$), 31.64-(C$_{3''}$), 29.97 (C$_{23}$), 29.13 (C$_2$), 21.63 (C$_{11}$), 20.05 (C$_{27}$), 19.87 (C$_{19}$), 18.90 (C$_{21}$), 17.39 (C$_{18}$)

Compound 102: 3-O-{3-[4-(α-L-rhamnopyranosyloxymethyl)-1,2,3-triazol-1-yl]propyl}solanidine of formula

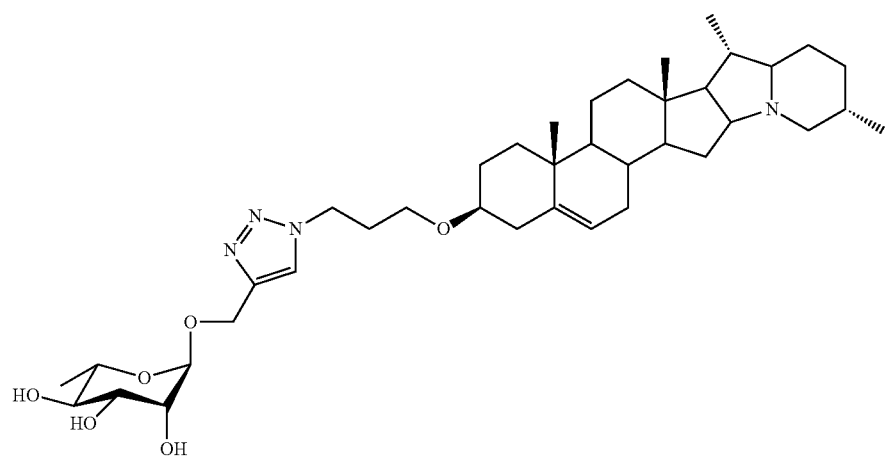

Compound 75 (0.08 mmol, 40 mg) and compound 10 (0.10 mmol, 20 mg) are dissolved in 3.75 ml of a mixture of 1,4-dioxane and $H_2O$ (4:1 by volume). Copper(II) sulfate (0.12 mmol, 19 mg) and sodium ascorbate (0.23 mmol, 47 mg) are then added. The reaction medium is stirred at 80° C. for 24 hours. The mixture is filtered through Celite and the collected filtrate is concentrated under reduced pressure. The residue is purified by CPC. Compound 102 is obtained with a yield of 52% (28 mg).

Appearance: yellow oil

M: 682.93 g·mol$^{-1}$

Empirical formula: $C_{35}H_{62}N_4O_6$

Rf: 0.34 ($CHCl_3$/MeOH: 80:20)

$[\alpha]_D^{20}$: −33.30 (c=0.1, MeOH)

HRMS: 683.4735 (683.4748 calculated for $C_{39}H_{63}N_4O_6$)

FT-IR (ATR in cm$^{-1}$): 3379 (uO—H), 2955-2854-(uC—H), 1076-1011 (uC—O)

$^1$H NMR (pyridine-d$_5$, 600 MHz): 8.09 (s, 1H, H$_{Rha1'''}$), 5.52 (s, 1H, H$_{Rha1}$), 5.43 (d, J=2.8 Hz, 1H, H$_6$), 5.19 (d, 1H, $^2J_{1'a,1'b}$=12.1 Hz, H$_{Rha1'a}$), 4.97 (d, 1H, $^2J_{1'b,1'a}$=12.1 Hz, H$_{Rha1'b}$), 4.57 (m, 3H, H$_{3'''}$ and H$_{Rha2}$), 4.51 (d, 1H, J=6.5 Hz, H$_{Rha3}$ or H$_{Rha4}$), 4.31 (m, 2H, H$_{Rha5}$ and H$_{Rha3}$ or H$_{Rha4}$), 3.42 (m, 2H, H$_{3'}$), 3.17 (m, 1H, H$_3$), 2.96 (d, 1H, J=7.6 Hz, H$_{26a}$), 2.71 (m, 1H, H$_{16}$), 2.49 (d, 1H, J=12.8 Hz, H$_{4a}$), 2.36 (t, 1H, J=11.8 Hz, H$_{4b}$), 2.16 (m, 2H, H$_{3'''}$), 2.04-(d, 1H, J=8.3 Hz), 1.94-(d, 1H, J=11.9 Hz), 1.81-1.27 (m, 12H), 1.14-(m, 2H), 0.99 (m, 9H, H$_{18}$, H$_{19}$ and H$_{21}$), 0.91 (m, 4H), 0.84-(d, 3H, $^3J_{27,26}$=10.8 Hz, H$_{27}$)

$^{13}$C NMR (pyridine-d$_5$, 150 MHz): 145.30 (C$_{Rha''}$), 141.41 (C$_5$), 124.21 (C$_{Rha1'''}$), 122.18 (C$_6$), 101.39 (C$_{Rha1}$), 79.67 (C$_3$), 75.18 (C$_{22}$), 74.35 (C$_{Rha3}$, C$_{Rha4}$ or C$_{Rha5}$), 73.13 (C$_{Rha3}$, C$_{Rha4}$ or C$_{Rha5}$), 72.59 (C$_{Rha2}$), 70.47 (C$_{Rha3}$, C$_{Rha4}$ or C$_{Rha5}$), 69.68 (C$_{16}$), 64.65 (C$_{3'}$), 62.10 (C$_{17}$), 61.07 (C$_{Gal1'}$), 60.60 (C$_{26}$), 58.15 (C$_{14}$), 50.87 (C$_9$), 47.94-(C$_{3'''}$), 40.95 (C$_{13}$), 40.47 (C$_{12}$), 39.94-(C$_4$), 37.76 (C$_1$), 37.57 (C$_{10}$), 37.28 (C$_{20}$), 32.78 (C$_8$), 32.30 (C$_7$), 31.77 (C$_{25}$), 31.65 (C$_{3''}$), 31.15 (C$_{15}$ or C$_{24}$), 30.74-(C$_{15}$ or C$_{24}$), 30.37 (C$_{23}$), 29.13 (C$_2$), 21.63 (C$_{11}$), 20.02 (C$_{27}$), 19.95 (C$_{Rha6}$), 19.87 (C$_{19}$), 19.03 (C$_{21}$), 17.39 (C$_{18}$)

Compound 103: 3-O-{3-[4-(α-L-rhamnopyranosyl-thiomethyl)-1,2,3-triazol-1-yl]propyl}solanidine of formula

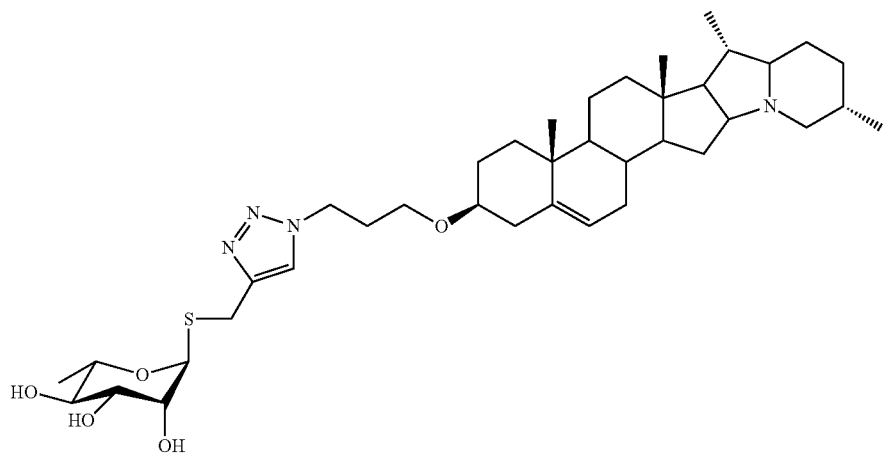

Compound 75 (0.08 mmol, 40 mg) and compound 19 (0.10 mmol, 22 mg) are dissolved in 3.75 ml of a mixture of 1,4-dioxane and $H_2O$ (4:1 by volume). Copper(II) sulfate (0.12 mmol, 19 mg) and sodium ascorbate (0.23 mmol, 47 mg) are then added. The reaction medium is stirred at 80° C. for 24 hours. The mixture is filtered through Celite and the collected filtrate is concentrated under reduced pressure. The residue is purified by CPC. Compound 103 is obtained with a yield of 63% (purity not confirmed by NMR).

Appearance: brown syrup

M: 699.00 g·mol$^{-1}$

Empirical formula: $C_{39}H_{62}N_4O_5S$ $[\alpha]_D^{20}$: +3° (c=0.1, MeOH)

HRMS: 699.4515 (699.4519 calculated for $C_{39}H_{63}N_4O_5S$)

FT-IR (ATR in cm$^{-1}$): 3383 (uO—H), 2926 (uC—H), 1122-1010 (uC—O)

Compound 104: 3-O-(3-{4-[1-thio-α-L-rhamnopyranosyl-(1→4)-β-D-glucopyranosyloxymethyl]-1,2,3-triazol-1-yl}propyl)solanidine of formula

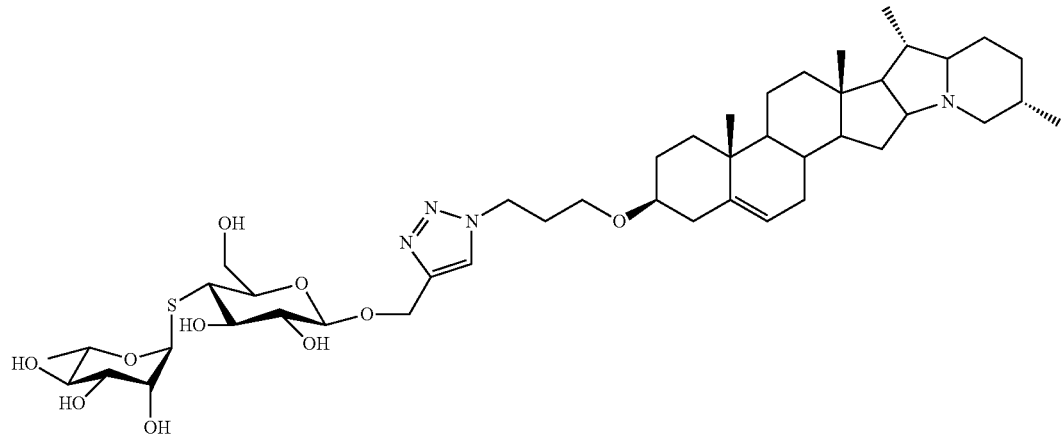

Compound 75 (0.08 mmol, 40 mg) and compound 28 (0.10 mmol, 38 mg) are dissolved in 3.75 ml of a mixture of 1,4-dioxane and $H_2O$ (4:1 by volume). Copper(II) sulfate (0.12 mmol, 19 mg) and sodium ascorbate (0.23 mmol, 47 mg) are then added. The reaction medium is stirred at 80° C. for 24 hours. The mixture is filtered through Celite and the collected filtrate is concentrated under reduced pressure. The residue is purified by CPC. Compound 104 is obtained with a yield of 59% (purity not confirmed by NMR).

Appearance: brown syrup
M: 861.14 g·mol$^{-1}$

Empirical formula: $C_{45}H_{72}N_4O_{10}S$
$[\alpha]_D^{20}$: −38.2° (c=0.1, MeOH)
HRMS: 861.5039 (861.5047 calculated for $C_{45}H_{73}N_4O_{10}S$)
FT-IR (ATR in cm$^{-1}$): 3339 (uO—H), 2935-2877 (uC—H), 1056 (uC—O)

Compound 105: 3-O-[3-(4-{[(α-L-rhamnopyranosyl)-(1→4)]-[(α-L-rhamnopyranosyl)-(1→2)]-β-D-glucopyranosyloxymethyl}-1,2,3-triazol-1-yl)propyl]solanidine of formula

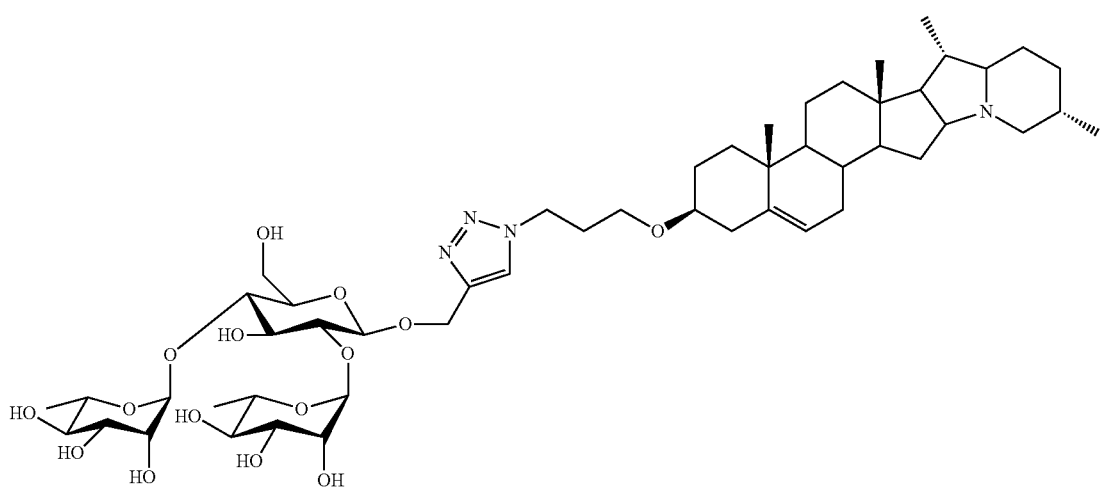

Compound 75 (0.08 mmol, 40 mg) and compound 56 (0.10 mmol, 51 mg) are dissolved in 3.75 ml of a mixture of 1,4-dioxane and $H_2O$ (4:1 by volume). Copper(II) sulfate (0.12 mmol, 19 mg) and sodium ascorbate (0.23 mmol, 47 mg) are then added. The reaction medium is stirred at 80° C. for 24 hours. The mixture is filtered through Celite and the collected filtrate is concentrated under reduced pressure. The residue is purified by CPC. Compound 105 is obtained with a yield of 67% (purity not confirmed by NMR).

Appearance: brown syrup

M: 991.21 g·mol$^{-1}$

Empirical formula: $C_{51}H_{82}N_4O_{15}$ $[\alpha]_D^{20}$: −19.5° (c=0.1, MeOH)

HRMS: 991.5820 (991.5855 calculated for $C_{51}H_{83}N_4O_{15}$)

FT-IR (ATR in cm$^{-1}$): 3347 (uO—H), 2931 (uC—H), 1126-980 (uC—O)

Example 2 Biological Tests 2-1. Insects

The *Macrosiphum euphorbiae* population was initiated from an apterous female provided by the Laboratory of Functional Biology, Insects and Interactions of the INRA/INSA of Villeurbanne in 2004. She was captured in 1995 on an eggplant in the Rhone-Alps region. The *Macrosiphum euphorbiae* aphids were raised on Desiree variety potato plants indoors at 20±1° C., 60±5% relative humidity and under a photoperiod of 16 hours of light and 8 hours of darkness.

2-2. Physiological Monitoring

For the tests on *Macrosiphum euphorbiae* larvae, adults were isolated and placed in PVC cages on artificial medium for one day in order to synchronize their lineage. Neonates (40 per experiment), less than 24 hours old, are placed in PVC cages containing artificial medium alone (control experiment) or artificial medium supplemented with 0.002, 0.02 or 0.2 mM active compound.

For the tests on *Macrosiphum euphorbiae* adults, neonates (50 per experiment) resulting from synchronization are raised in petri dishes on leaves of Desiree variety potato plants for 10 days. Once the adult stage is reached, they are placed in PVC cages containing artificial medium alone (control experiment) or artificial medium supplemented with 0.002, 0.02 or 0.2 mM active compound.

The individuals were monitored every two days over a period of 16 days. With each recording, the artificial medium is changed. Each cage houses five aphids.

2-3. Artificial Medium

A standard diet was used as the basis for carrying out the physiological monitoring. Its composition was described by Febvay et al. (*J. Zool.* 1988, 66(11), 2449-2453) and then modified according to the conditions of Down et al. (*J. Insect Physiol.* 1996, 42(11-12), 1035-1045) as shown in Table 2. The medium is supplemented with active compound and placed between two layers of Parafilm® in sterile conditions.

TABLE 2

Protocol for obtaining artificial medium suitable for *Macrosiphum euphorbiae*

| Vitamins | mg |
|---|---|
| 4-Aminobenzoic acid | 100.00 |
| Ascorbic acid | 1000.00 |
| Biotin | 1.00 |
| $CaCl_2$ | 50.00 |
| Choline chloride | 500.00 |
| Folic acid | 10.00 |
| Myo-inositol | 420.00 |
| Nicotinic acid | 100.00 |
| Pyridoxine | 25.00 |
| Thiamine | 25.00 |

| Amino acids | mg |
|---|---|
| Alanine | 178.70 |
| β-D-Alanine | 6.22 |
| Arginine | 244.90 |
| Asparagine | 298.50 |
| Aspartic acid | 88.25 |
| Cysteine | 29.59 |
| Glutamic acid | 149.30 |
| Glutamine | 445.60 |
| Glycine | 166.50 |
| Histidine | 136.00 |
| Isoleucine | 164.70 |
| Leucine | 231.50 |
| Lysine | 351.00 |
| Methionine | 72.35 |
| Ornithine | 9.41 |
| Phenylalanine | 293.00 |
| Proline | 129.30 |
| Serine | 124.20 |
| Threonine | 127.10 |
| Tryptophan | 42.75 |
| Tyrosine | 38.63 |
| Valine | 190.80 |

| Trace metals | mg |
|---|---|
| $CuSO_4 \cdot 5H_2O$ | 0.47 |
| $FeCl_3 \cdot 6H_2O$ | 4.45 |
| $MnCl_2 \cdot 4H_2O$ | 0.65 |
| NaCl | 2.54 |
| $ZnCl_2$ | 0.83 |

| Sugar | g |
|---|---|
| Sucrose | 20 |

| Other compounds | mg |
|---|---|
| $CaCl_2$ | 3.00 |
| Citric acid | 5.80 |
| Cholesteryl benzoate | 2.50 |
| $MgSO_4 \cdot 7H_2O$ | 242.00 |

Preparation of the vitamins:

1-Weigh the vitamins and place them in a beaker.
2-Add 150 ml of sterile water.
3-Add 5 mg of riboflavin (dissolved in 1 ml of sterile water while heating at 50° C.).
4-Adjust the volume to 200 ml.
5-Prepare 10 ml aliquots and store at −20° C.

Preparation of the artificial medium

1-Weigh the amino acids, sugar, metals and other compounds.
2-Add 40 ml of sterile water and 20 ml of the vitamin mixture.
3-Dissolve for 2-3 hours with magnetic stirring.
4-Adjust the pH to 7 by adding 1M KOH solution (0.56 g in 10 ml of water) dropwise.
5-Add 250 mg of $KH_2PO_4$.
6-Adjust to 100 ml and pH 7.5.

2-4. Statistical Analyses

The statistical analyses were performed using the Statistica 10 software (StatSoft®). To compare aphid survival in comparison with the control, Pearson's $X^2$ test ($\alpha<0.05$) was applied. To compare the compounds in terms of concentration and nature, Fisher's least significant difference (LSD) test was applied ($\alpha<0.05$). Daily fecundity was also studied using Fisher's LSD test ($\alpha<0.05$).

2-5. Effects on Larval Survival

The biological tests were carried out on *Macrosiphum euphorbiae* neonates less than 24 hours old. They are placed on artificial medium containing chaconine, solanine, solanidine, 100, 101 or 102.

Figure 1B:
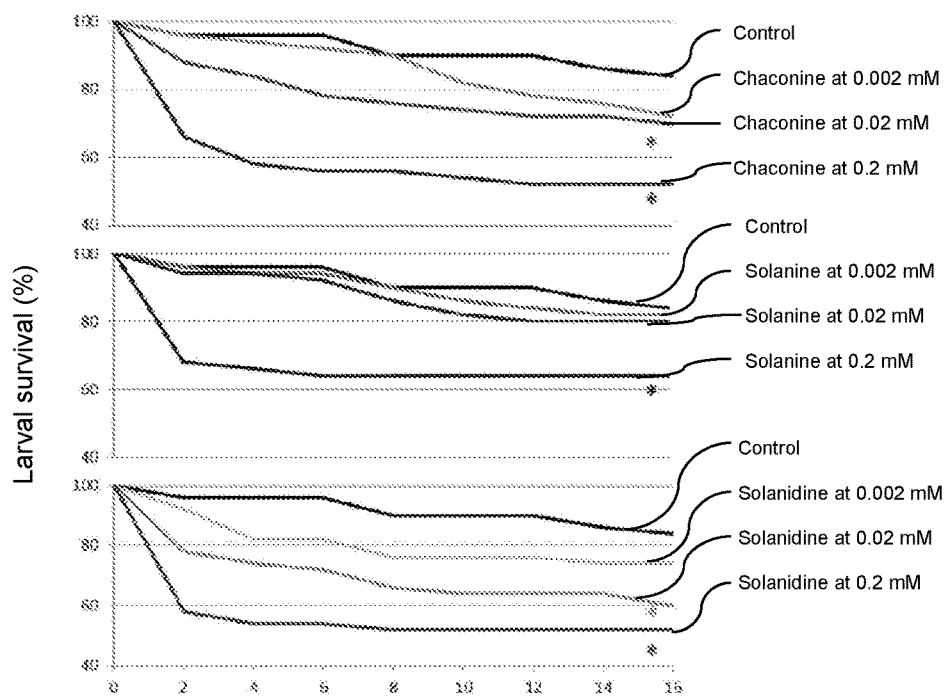
FIG. 1B shows the effects of chaconine, solanine and solanidine on *Macrosiphum euphorbiae* larvae survival, wherein the results were analyzed using Pearson's $X^2$ test; $\alpha=0.05$; *=significantly different from the control.

FIGS. 2A and 2B show the variation in mortality over time. FIG. 1A shows the effects on larval survival of compounds 100, 101 and 102 according to the invention. The results were analyzed using Pearson's $X^2$ test, wherein $\alpha=0.05$, * indicates that there is a significant difference in comparison with the control. FIG. 1B shows the effects on larval survival of chaconine, solanine and solanidine. The results were analyzed using Pearson's $X^2$ test, wherein $\alpha=0.05$, * indicates that there is a significant difference in comparison with the control.

According to these results, the aphicide activity of the synthetic glycoalkaloids is marked in comparison with the control. Moreover, the same is true with respect to 0.2 mM solanidine, which shows the best result among the natural molecules. Generally, 0.002 mM synthetic glycoalkaloids have lower activity than 0.2 mM solanidine ($p<0.001$ for compounds 100 and 102 and $p=0.006$ for compound 101). If the concentrations of 100, 101 and 102 are increased to 0.02 mM, the survival rates are 26%, 33% and 32%, respectively. At this concentration, the aphicide properties with respect to larvae become stronger than with solanidine. This observation is even more marked for the 0.2 mM concentrations, where larval survival is 22%, 24% and 6% for 100, 101 and 102, respectively ($p<0.001$).

The results of this test after 16 days of treatment are presented in Table 3 below. The values are expressed as a percentage. Obviously, the lower the value, the more powerful the compounds. As Table 3 shows, the compounds according to the invention have very low values compared with the natural glycoalkaloids. Consequently, the very powerful aphicide effects of the compounds according to the invention compared with natural glycoalkaloids were shown.

TABLE 3

Percentage of larval survival for each experiment after 16 days of treatment. Values followed by the same letter indicate that there is no significant difference according to Pearson's test with Bonferroni correction ($\alpha = 0.005$) or Fisher's LSD test ($\alpha = 0.005$).

|  | 0.002 mM | 0.02 mM | 0.2 mM |
| --- | --- | --- | --- |
| 100 | 76a | 26b | 22c |
| 101 | 62a | 33b | 24c |
| 102 | 84a | 32b | 6d |
| Chaconine | 72a | 70a | 52b |
| Solanine | 82a | 80a | 64c |
| Solanidine | 74a | 60d | 52b |

2-6. Effects on Adult Survival

Figure 2:
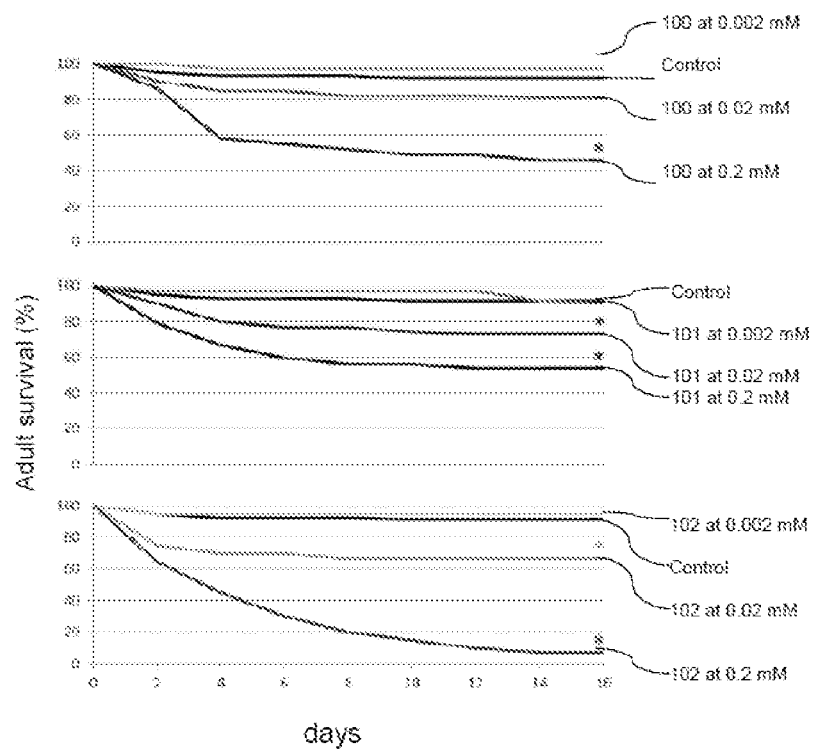
FIG. 2 shows the effects of compounds according to the invention on *Macrosiphum euphorbiae* adults, wherein the results were analyzed using Pearson's $X^2$ test; $\alpha=0.05$; *=significantly different from the control.

The biological tests of compounds 100, 101 and 102 on *Macrosiphum euphorbiae* adults are presented in FIG. 2, and are compared to a control experiment.

Compound 100 has no significant activity in comparison with the control at concentrations of 0.002 mM and 0.02 mM. However, a notable effect is observed at 0.2 mM ($p<0.001$) with a mortality rate of 54%. Concerning compound 101, an increase in the concentration to 0.02 and 0.2 mM makes it possible to observe a drop in the survival rate of *Macrosiphum euphorbiae* adults ($p=0.006$ and $p<0.001$, respectively). Lastly, compound 102 has no significant aphicide activity at the lowest concentration, but, just like compound 101, an increase in the concentration of the compound to 0.02 and 0.2 mM makes it possible to observe a marked effect on the survival of adults ($p<0.001$ for both experiments).

The results of this test after 16 days of treatment are presented in Table 4 below. The values are expressed as a percentage. As Table 4 shows, the compounds according to the invention have very low values in comparison with the control.

TABLE 4

Percentage of adult survival after 16 days of treatment. Values followed by the same letter indicate that there is no significant difference according to Fisher's LSD test ($\alpha = 0.005$).

|  | 0.002 mM | 0.02 mM | 0.2 mM |
| --- | --- | --- | --- |
| 100 | 97a | 81b | 46c |
| 101 | 90a | 73b | 54c |
| 102 | 95a | 67b | 7d |

2-7. Effects on Reproduction

Figure 3:
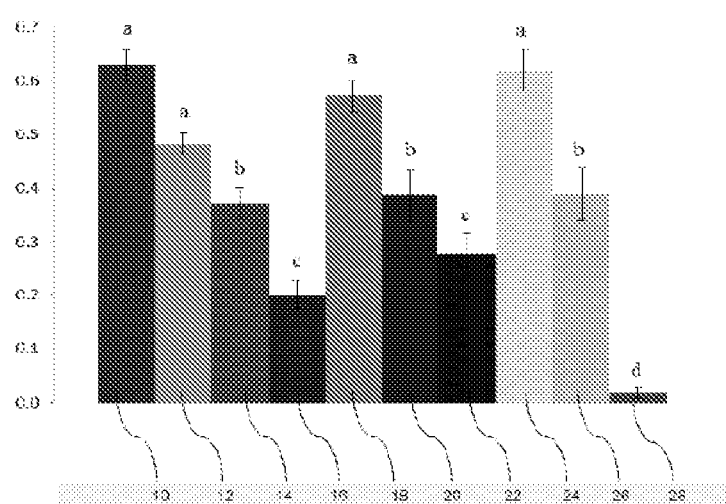
FIG. 3 shows the effects of compounds according to the invention on *Macrosiphum euphorbiae* reproduction.

Data regarding the number of larvae resulting from parthenogenesis can be used to calculate daily fecundity per aphid. The results are presented in FIG. 3, wherein the number 10 represents the control, the reference numbers 12, 14 and 16 represent the results of compound 100 at the concentrations of 0.002, 0.02 and 0.2 mM, respectively, the reference numbers 18, 20 and 22 represent the results of compound 101 at the concentrations of 0.002, 0.02 and 0.2 mM, respectively, the reference numbers 24, 26, and 28 represent the results of compound 102 at the concentrations of 0.002, 0.02 and 0.2 mM, respectively.

As for survival rate, the presence in the artificial medium of the compounds according to the invention can have an impact on reproduction. In comparison with the control experiment, compounds 100, 101 and 102 at concentrations of 0.02 and 0.2 mM significantly reduce reproduction ($p<0.001$).

CONCLUSION

As described in detail above, the compounds according to the invention have the following advantages:

The structural changes provided by the synthesis make it possible to increase the toxicity of glycoalkaloids, in particular on *Macrosiphum euphorbiae* larvae or adults.

The compounds according to the invention could be used as insecticides against other potato-infesting species but also against insects not specific to this plant.

Unlike natural glycoalkaloids, in which a trisaccharide is essential, a single saccharide unit would be sufficient to generate aphicide activity with the compounds according to the invention.

The compounds according to the invention have a structure that is relatively simple and easy to synthesize.

The compounds according to the invention have insecticidal properties (insect behavior is not affected, but the compound acts on demographic parameters like survival and reproduction).—The compounds according to the invention can be obtained from chaconine and from solanine, themselves obtained from coproducts of the potato industry, which makes it possible to exploit them.

Lastly, the compounds according to the invention have other possible activities, such as bactericidal, fungicidal, nematicidal, antiviral or antitumoral properties.

What is claimed is:

1. A compound of formula (I):

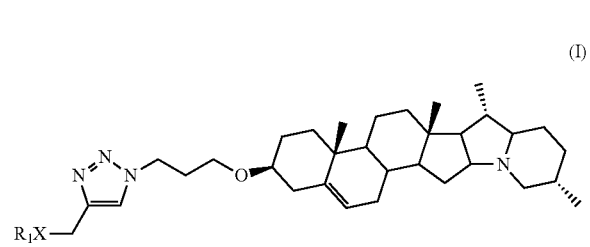

wherein:
X is an oxygen atom or a sulfur atom; and
R₁ represents a group comprising 1 to 10 saccharide unit(s), each saccharide unit corresponding to any hexose and/or any pentose.

2. The compound of formula (I) as claimed in claim 1, wherein said saccharide unit is a hexose.

3. The compound of formula (I) as claimed in claim 1, wherein R₁ is selected from the group consisting of a glucosyl group, a galactosyl group and a rhamnosyl group.

4. The compound of formula (I) as claimed in claim 1, wherein R₁ is a monosaccharide, a disaccharide, a thiodisaccharide, a trisaccharide or a thiotrisaccharide.

5. The compound of formula (I) as claimed in claim 1, wherein X is an oxygen atom.

6. The compound of formula (I) as claimed in claim 1, wherein X is a sulfur atom.

7. A compound of formula (II):

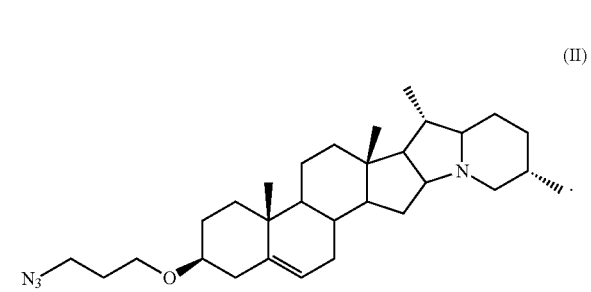 [SMILES: C[C@H]1CCC2[C@@H](C)C3C(CC4C5CC=C6C[C@@H](OCCCN=[N+]=[N-])CC[C@]6(C)C5CC[C@@]43C)N2C1 ; "."]

8. An insecticide comprising the compound of formula (I) as claimed in claim 1.

9. A material selected from the group consisting of as an antibacterial, an antifungal, a nematicide and an antiviral, said material comprising the compound of formula (I) as claimed in claim 1.

10. A medicine comprising the compound of formula (I) as claimed in claim 1.

11. A method for obtaining the compound of formula (I) as claimed in claim 1, comprising the steps of:
a) providing a compound of formula (II):

and
b) reacting the compound of formula (II), in the presence or absence of a catalyst, with a compound of formula (III):

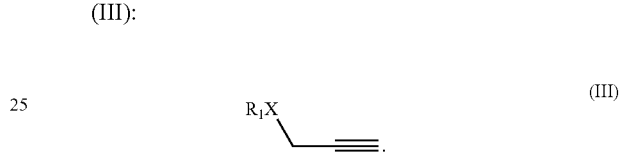

12. The method for obtaining the compound of formula (I) as claimed in claim 11, further comprising the steps of:
c) providing a compound of formula (IV):

wherein Ts is a tosyl group;
d) providing a compound of formula (V):

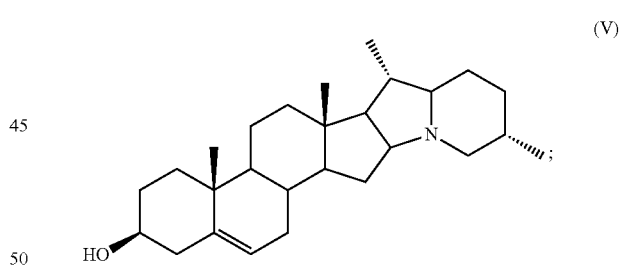

and
e) reacting the compound of formula (V) with the compound of formula (IV) in order to obtain the compound of formula (II).

13. The method for obtaining the compound of formula (I) as claimed in claim 11, wherein said catalyst is selected from ruthenium compounds or copper compounds.

14. A composition comprising the compound of formula (I) as claimed in claim 1.

* * * * *